(12) United States Patent
Rajasekaran et al.

US011327068B2

(10) Patent No.: US 11,327,068 B2
(45) Date of Patent: *May 10, 2022

(54) METHOD AND APPARATUS FOR DETERMINING A PRESENCE OF A MICROORGANISM IN A SAMPLE

(71) Applicant: University of Central Florida Research Foundation, Inc., Orlando, FL (US)

(72) Inventors: Parthiban Rajasekaran, Orlando, FL (US); Swaminathan Rajaraman, Winter Park, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 343 days.

This patent is subject to a terminal disclaimer.

(21) Appl. No.: 15/952,158

(22) Filed: Apr. 12, 2018

(65) Prior Publication Data

US 2018/0372711 A1    Dec. 27, 2018

Related U.S. Application Data

(60) Provisional application No. 62/484,521, filed on Apr. 12, 2017.

(51) Int. Cl.
| | | |
|---|---|---|
| *G01N 33/483* | (2006.01) | |
| *C12N 1/20* | (2006.01) | |
| *A61B 5/00* | (2006.01) | |
| *H01L 31/0224* | (2006.01) | |
| *B01L 3/00* | (2006.01) | |
| *A61B 5/1468* | (2006.01) | |

(52) U.S. Cl.
CPC .......... *G01N 33/4836* (2013.01); *A61B 5/00* (2013.01); *B01L 3/502715* (2013.01); *H01L 31/022458* (2013.01); *A61B 5/1468* (2013.01); *B01L 2300/0645* (2013.01); *C12N 1/20* (2013.01)

(58) Field of Classification Search
CPC .... G01N 33/4836; A61B 5/00; A61B 5/1468; H01L 31/022458; C12N 1/20
See application file for complete search history.

(56) References Cited

U.S. PATENT DOCUMENTS

| | | | |
|---|---|---|---|
| 5,965,452 A | | 10/1999 | Kovacs |
| 6,051,422 A | * | 4/2000 | Kovacs ............ G01N 33/48728 204/403.06 |
| 9,279,201 B2 | | 3/2016 | Rajaraman et al. |
| 9,279,797 B2 | | 3/2016 | Clements et al. |
| 9,290,756 B2 | | 3/2016 | Ross et al. |
| 9,329,168 B2 | | 5/2016 | Rajaraman et al. |
| 2003/0175687 A1 | * | 9/2003 | Tippet ...................... C12Q 1/04 435/5 |
| 2014/0303471 A1 | | 10/2014 | Rajaraman et al. |
| 2015/0125942 A1 | | 5/2015 | Grier, Jr. et al. |
| 2016/0047770 A1 | | 2/2016 | Tyler et al. |

OTHER PUBLICATIONS

Chuang, M-C. et al., Multifunctional microelectrode array (mMEA) chip for neural-electrical and neural-chemical interfaces: Characterization of comb interdigitated electrode towards dopamine detection, 2013, Biosensors and Bioelectronics, 41, 602-607 (Year: 2013).*
Masi E. et al., Electrical spiking in bacterial biofilms, 2015, Journal of the Royal Society Interface, 12: 20141036, 1-10 (Year: 2015).*
Mallén-Alberdi, M. et al., Impedance spectral fingerprint of *E. coli* cells on interdigitated electrodes: A new approach for label free and selective detection, 2016, Sensing and bio-sensing research, 7, 100-106 (Year: 2016).*
Manjunath, K.L. et al., Detection of 'Candidatus Liberibacter asiaticus' in Diaphorina citri and Its Importance in the Management of Citrus Huanglongbing in Florida, 2008, Phytopathology, 98(4), 387-396 (Year: 2008).*
Ausaf, A., et al., 3-D printing, ink casting and lamination (3-D PICL): A rapid, robust, and cost effective process technology toward the fabrication of microfluidic and biological devices, "MicroTAS", (2017).
Delcour, A., Electrophysiology of Bacteria, "Annual review of microbiology", pp. 179-197, vol. 67 (2013).
Jewett, K., et al., Feedback modulation of neural network synchrony and seizure susceptibility, "Molecular Brain", vol. 9 (2016).
Kalia, L. V. and A. E. Lang, Disease-modifying strategies for Parkinson's disease, "Lancet", pp. 896-912, vol. 386 (2015).
Kim, J., et al., Surface-modified microelectrode array with flake nanostructure for neural recording and stimulation, "Nanotech.", vol. 21 (2010).
Masi, E., et al., Electrical spiking in bacterial biofilms, "Journal of the Royal Society Interface", vol. 12, Issue 102 (2015).

(Continued)

*Primary Examiner* — Olivia M. Wise
*Assistant Examiner* — Anjali Ajit Hirani
(74) *Attorney, Agent, or Firm* — Timothy H. Van Dyke; Wolter, Van Dyke, Davis, PLLC

(57) ABSTRACT

A method and apparatus for determining a presence of a microorganism in a sample is provided. The method includes storing electrophysiological and/or impedance signatures of a plurality of microorganisms in a memory of a processor. The method also includes obtaining a sample and generating an electrophysiological and/or impedance signature of the sample. The electrophysiological and/or impedance signature of the sample is compared with the electrophysiological and/or impedance signatures in the memory. A presence of one of the plurality of microorganisms in the sample is then identified based on a correlation between the electrophysiological and/or impedance signature of the sample and the electrophysiological and/or impedance signature of the one of the plurality of microorganisms. A method is also provided for determining a growth stage of a microorganism in a sample.

14 Claims, 16 Drawing Sheets

(56) References Cited

OTHER PUBLICATIONS

Paredes, J., et al., Comparison of real time impedance monitoring of bacterial biofilm cultures in different experimental setups mimicking real field environments, "Sensors and Actuators B: Chemical" vol. 195 (2014).

Tyler, P.E and S. Rajaraman, A 48-well Transparent Microelectrode Array Fabricated utilizing a Flexible "Wrapped Around" Interconnect Technology, "IEEE Sensors Conference, Orlando, FL" (2016).

* cited by examiner

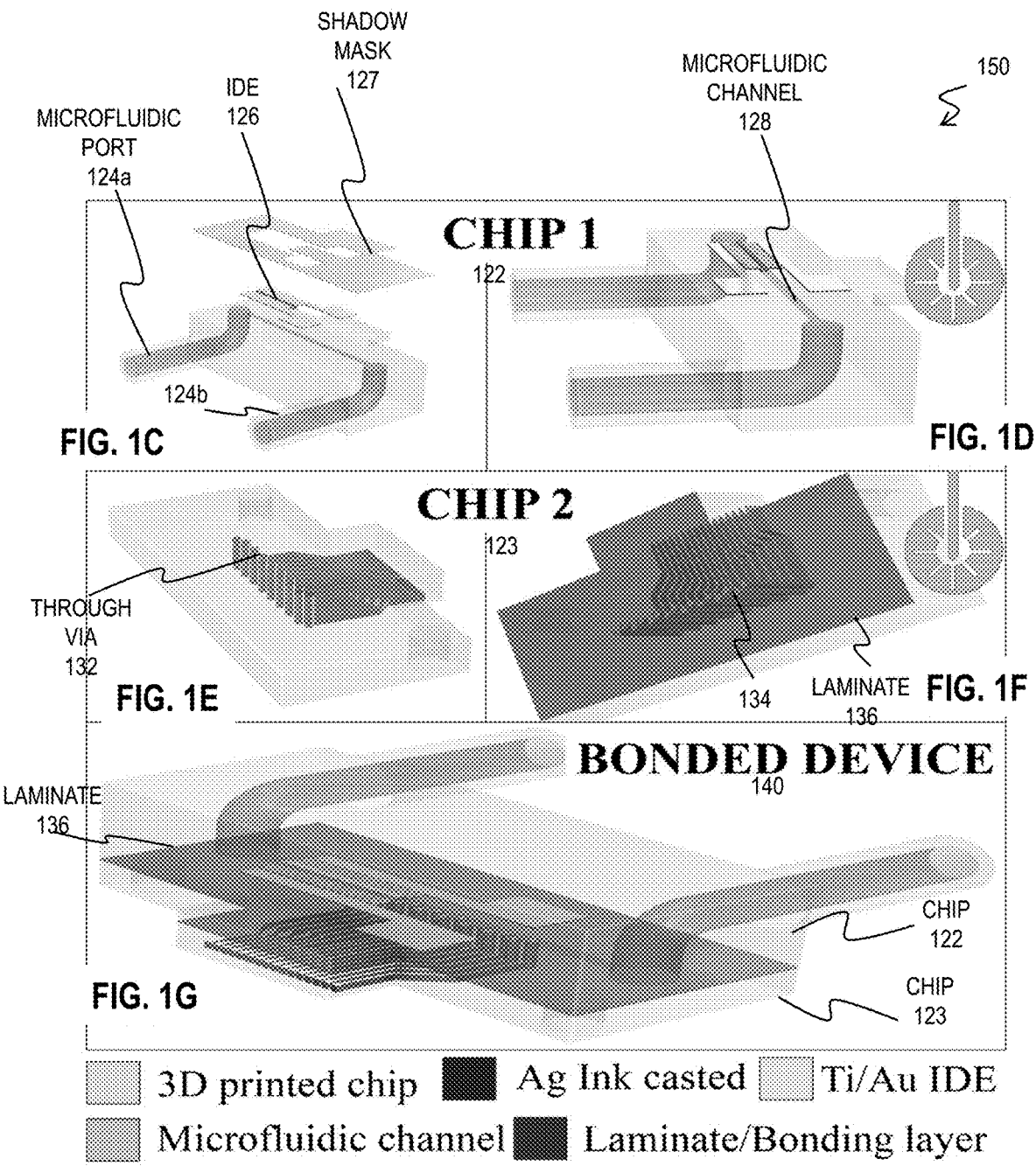

MICROFLUIDIC
CHANNEL
128

IDE
126

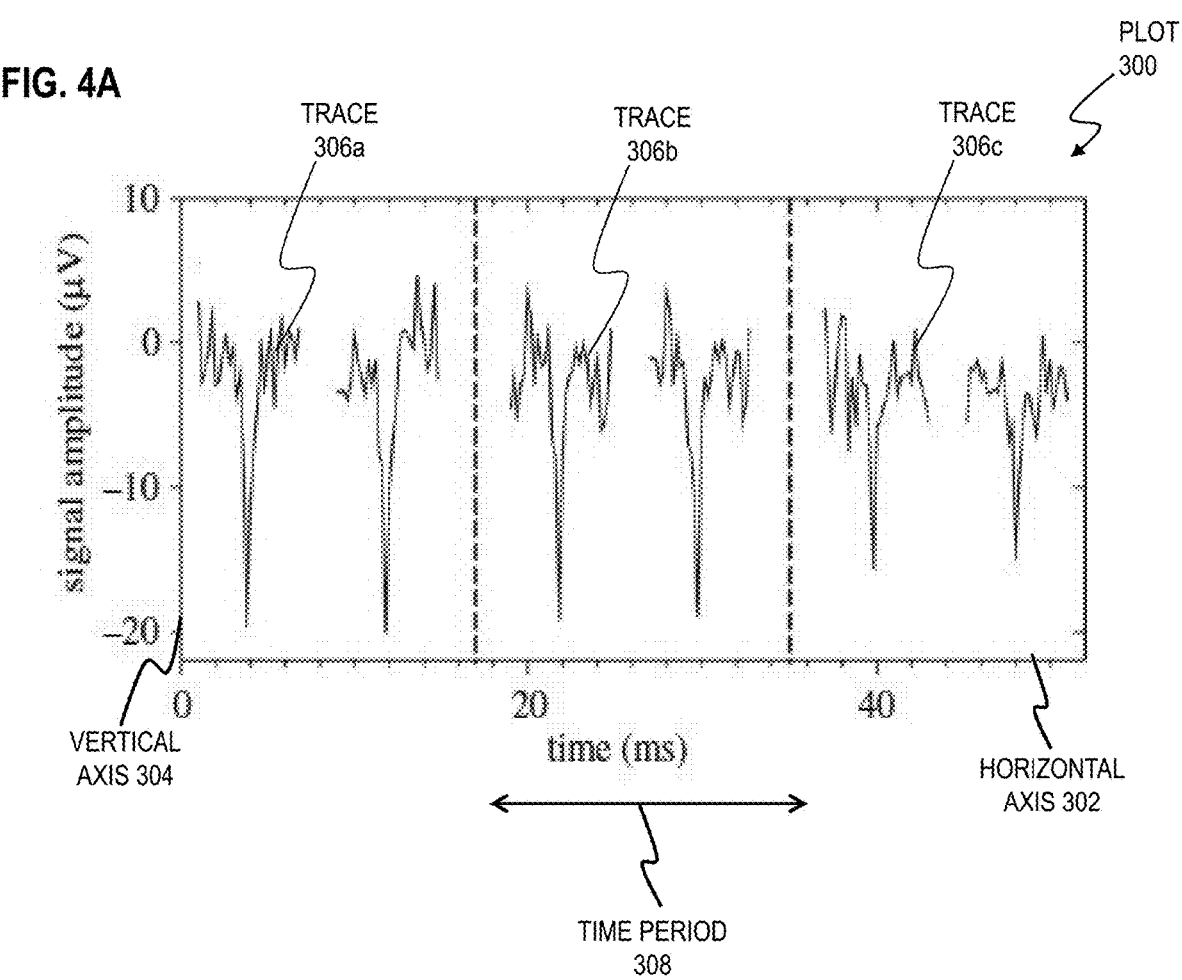

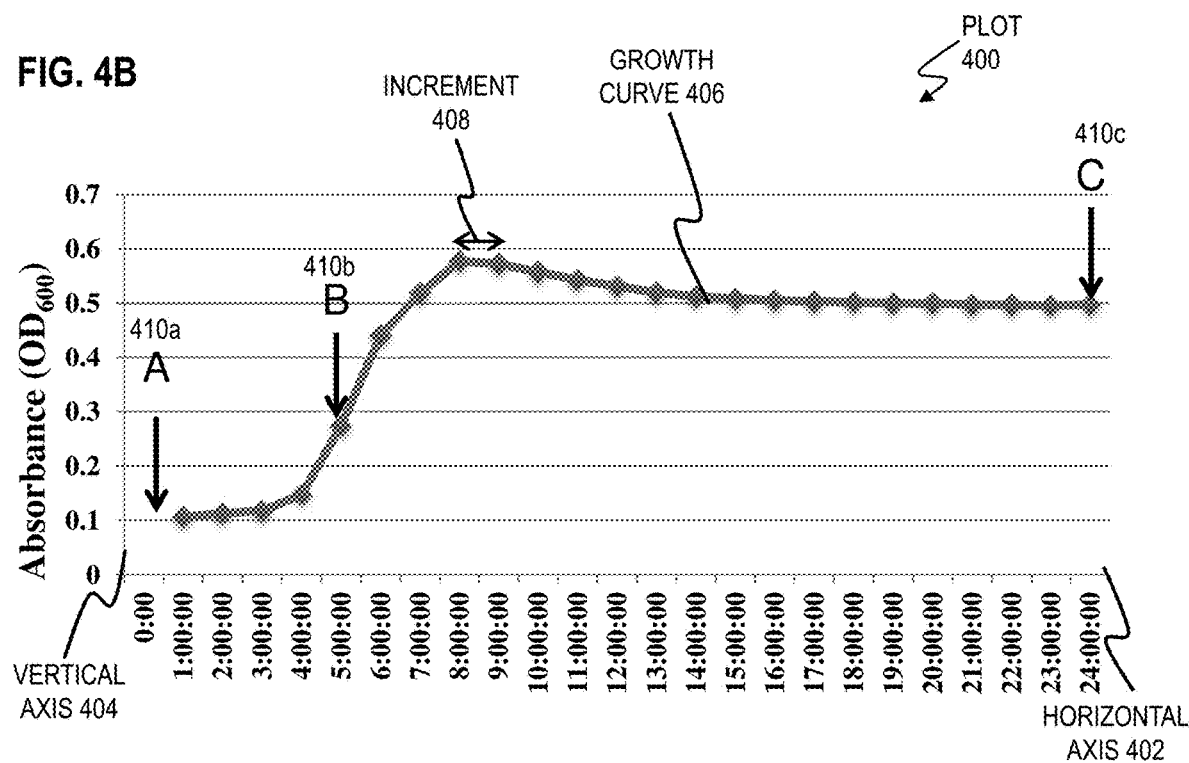
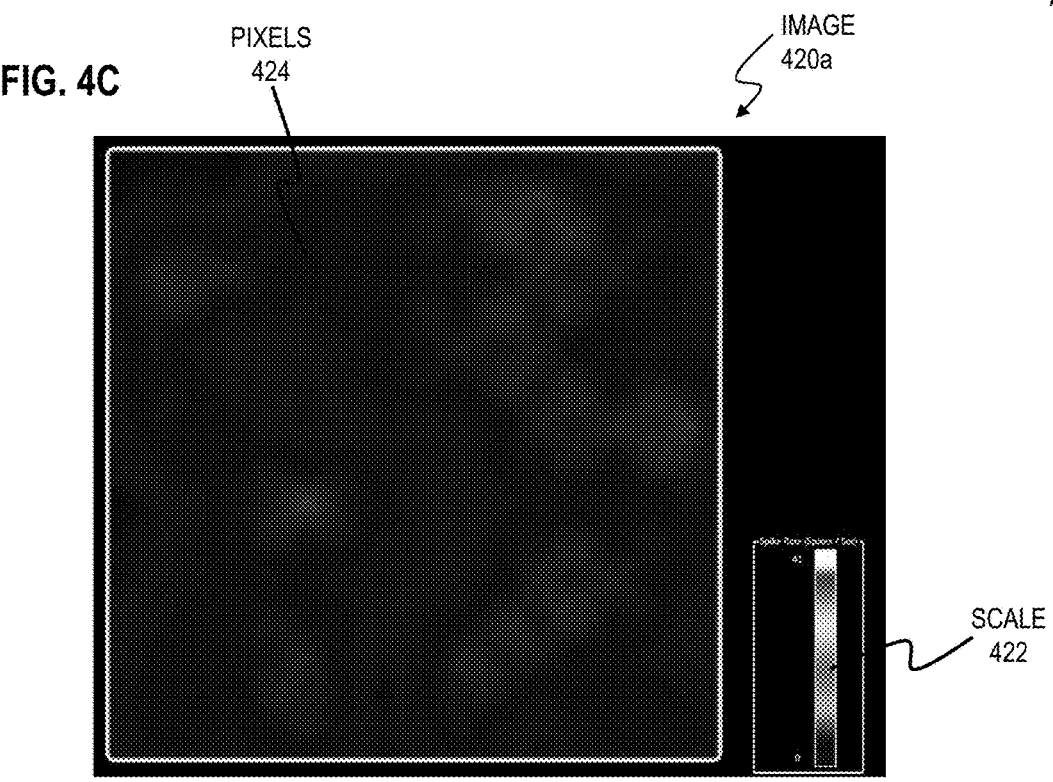

PLOT 450

VERTICAL AXIS 454

HORIZONTAL AXIS 452

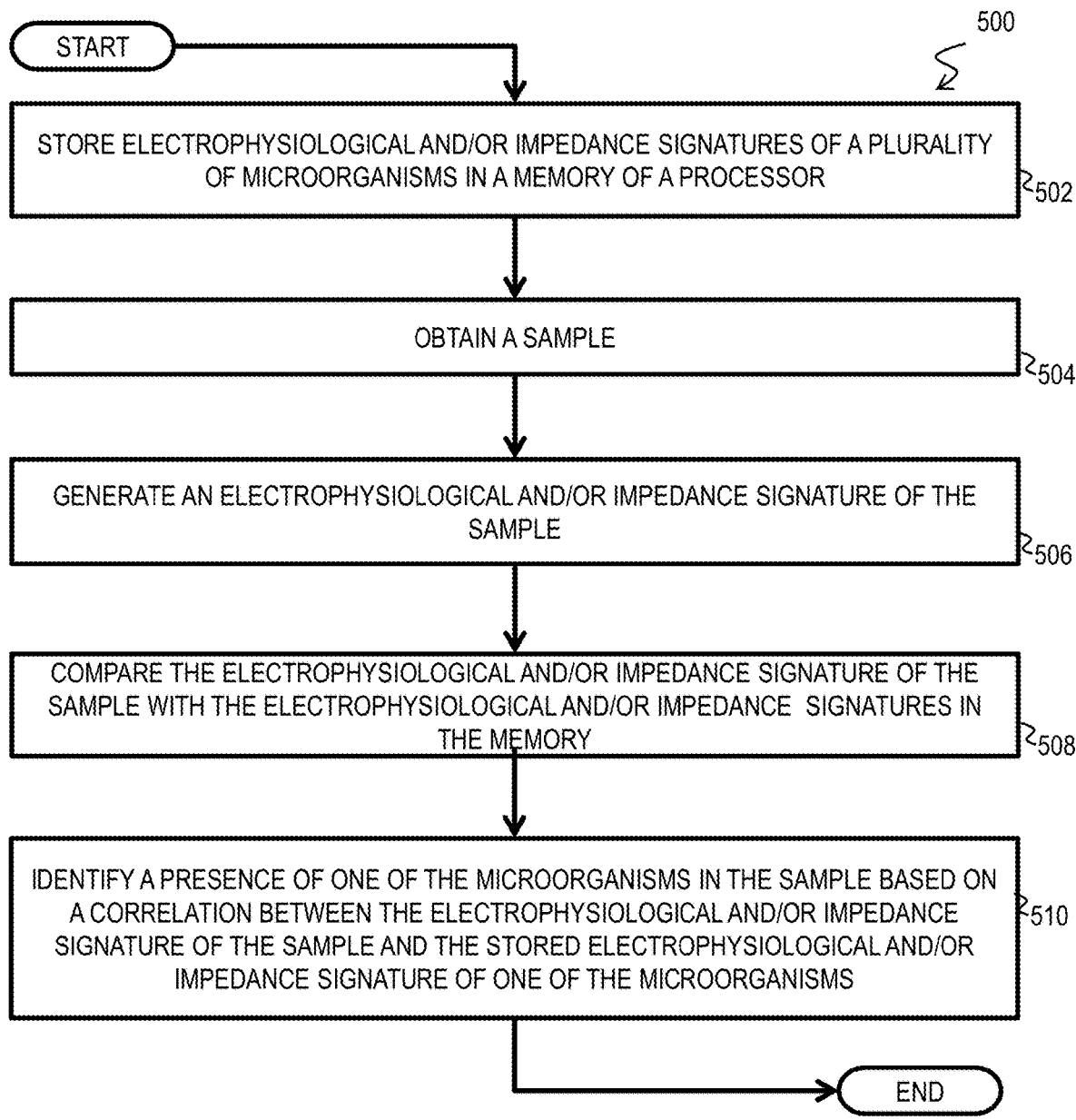

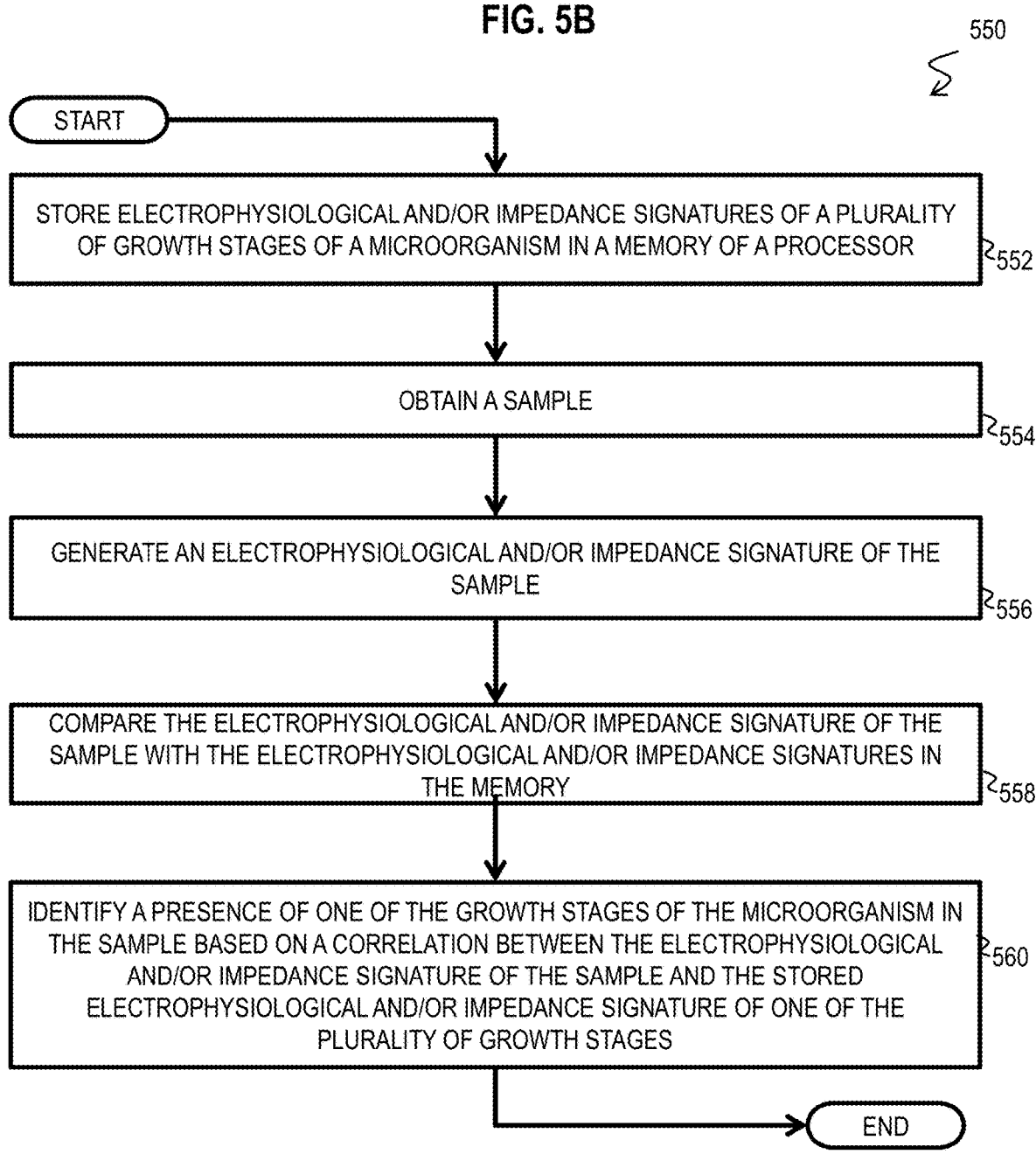

METHOD AND APPARATUS FOR DETERMINING A PRESENCE OF A MICROORGANISM IN A SAMPLE

CROSS-REFERENCE TO RELATED APPLICATIONS

This application claims benefit of Provisional Appln. 62/484,521, filed Apr. 12, 2017, the entire contents of which are hereby incorporated by reference as if fully set forth herein, under 35 U.S.C. § 119(e).

BACKGROUND

A disease is any disorder of a structure or function of an organism. Diseases may be caused by external factors such as pathogenic microorganisms that include viruses, bacterium, prion, and fungi.

One example of a known disease is Huanglongbing (HLB) that affects citrus trees and is caused by the phloem-limited bacterium *Candidatus Liberibacter asiaticus* (Las). HLB has reduced the production of citrus fruits in Florida to record low levels. Among the largest citrus producing states of Florida and California, most of Florida citrus groves are infected by HLB and California has started reporting sporadic incidence of HLB.

Another example of pathogenic microorganisms include the *Mycobacterium* genus of bacteria, such as *Mycobacterium tuberculosis* that is the causative agent of tuberculosis (TB) in humans and animals. Other species of *Mycobacterium* include *Mycobacterium bovis, Mycobacterium paratuberculosis* and other non-tubercle forming *Mycobacterium* spp.

SUMMARY

In a first set of embodiments, a method is provided for determining a presence of a microorganism in a sample. The method includes storing electrophysiological and/or impedance signatures of a plurality of microorganisms in a memory of a processor. The method also includes obtaining a sample and generating an electrophysiological and/or impedance signature of the sample with a plurality of electrodes. The method also includes comparing the electrophysiological and/or impedance signature of the sample with the electrophysiological and/or impedance signatures in the memory. The method also includes identifying a presence of one of the plurality of microorganisms in the sample based on a correlation between the electrophysiological and/or impedance signature of the sample and the electrophysiological and/or impedance signature of the one of the plurality of microorganisms.

In a second set of embodiments, a method is provided for determining a presence of a microorganism in a sample. The method includes exposing the sample to a plurality of electrodes and generating an electrophysiological and/or impedance signature of the sample. The method further includes comparing the electrophysiological and/or impedance signature of the sample with a database of electrophysiological and/or impedance signatures corresponding to a plurality of microorganisms. The method further includes identifying a presence of one of the plurality of the microorganisms in the sample.

In a third set of embodiments, a method is provided for determining a growth stage of a microorganism in a sample. The method includes storing electrophysiological and/or impedance signatures of a plurality of growth stages of the microorganism in a memory of a processor. The method also includes obtaining a sample and generating an electrophysiological and/or impedance signature of the sample with a plurality of electrodes. The method also includes comparing the electrophysiological and/or impedance signature of the sample with the electrophysiological and/or impedance signatures in the memory. The method also includes identifying a presence of one of the plurality of growth stages of the microorganism in the sample based on a correlation between the electrophysiological and/or impedance signature of the sample and the electrophysiological and/or impedance signature of the one of the plurality of growth stages.

In a fourth set of embodiments, a method is provided for determining a presence of a growth stage of a microorganism in a sample. The method includes exposing the sample to a plurality of electrodes and generating an electrophysiological and/or impedance signature of the sample. The method further includes comparing the electrophysiological and/or impedance signature of the sample with a database of electrophysiological and/or impedance signatures corresponding to a plurality of growth stages of the microorganism. The method further includes identifying a presence of one of the plurality of the growth stages of the microorganism in the sample.

In a fifth set of embodiments, an apparatus is provided for determining a presence of a microorganism in a sample. The apparatus includes a microelectrode array (MEA) and/or an interdigitated electrode (IDE) configured to generate a signal based on the sample being exposed to the MEA and/or the IDE. The apparatus further includes a processor and a memory including one or more sequences of instructions. The memory and the sequences of instructions are configured to, with the processor, cause the apparatus to perform one or more steps of any of the method embodiments previously discussed.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 1C is an image that illustrates an example of an exploded view of a first chip of a multi-modal biosensor of the system of FIG. 1A, according to an embodiment;

FIG. 1D is an image that illustrates an example of a perspective view of the first chip of FIG. 1C, according to an embodiment;

FIG. 1E is an image that illustrates an example of through vias formed in a second chip of a multi-modal biosensor of the system of FIG. 1A, according to an embodiment;

FIG. 1F is an image that illustrates an example of microelectrodes in the second chip of a multi-modal biosensor of the system of FIG. 1A, according to an embodiment;

FIG. 1G is an image that illustrates an example of the first chip of FIG. 1D laminated to the second chip of FIG. 1F, according to an embodiment;

FIG. 4A is an image that illustrates an example of traces of a potential signal from the MEA in FIG. 1A for different microorganism samples, according to an embodiment;

FIG. 4B is an image that illustrates an example of a growth curve of a bacteria, according to an embodiment;

FIG. 4C is an image that illustrates an example of electrical activity of the bacteria during a first stage of the growth curve of FIG. 4B, according to an embodiment;

FIG. 5A is a flow diagram that illustrates an example of a method for determining a presence of a microorganism in a sample, according to an embodiment;

FIG. 5B is a flow diagram that illustrates an example of a method for determining a growth of a microorganism in a sample, according to an embodiment;

DETAILED DESCRIPTION

Figure 1A:
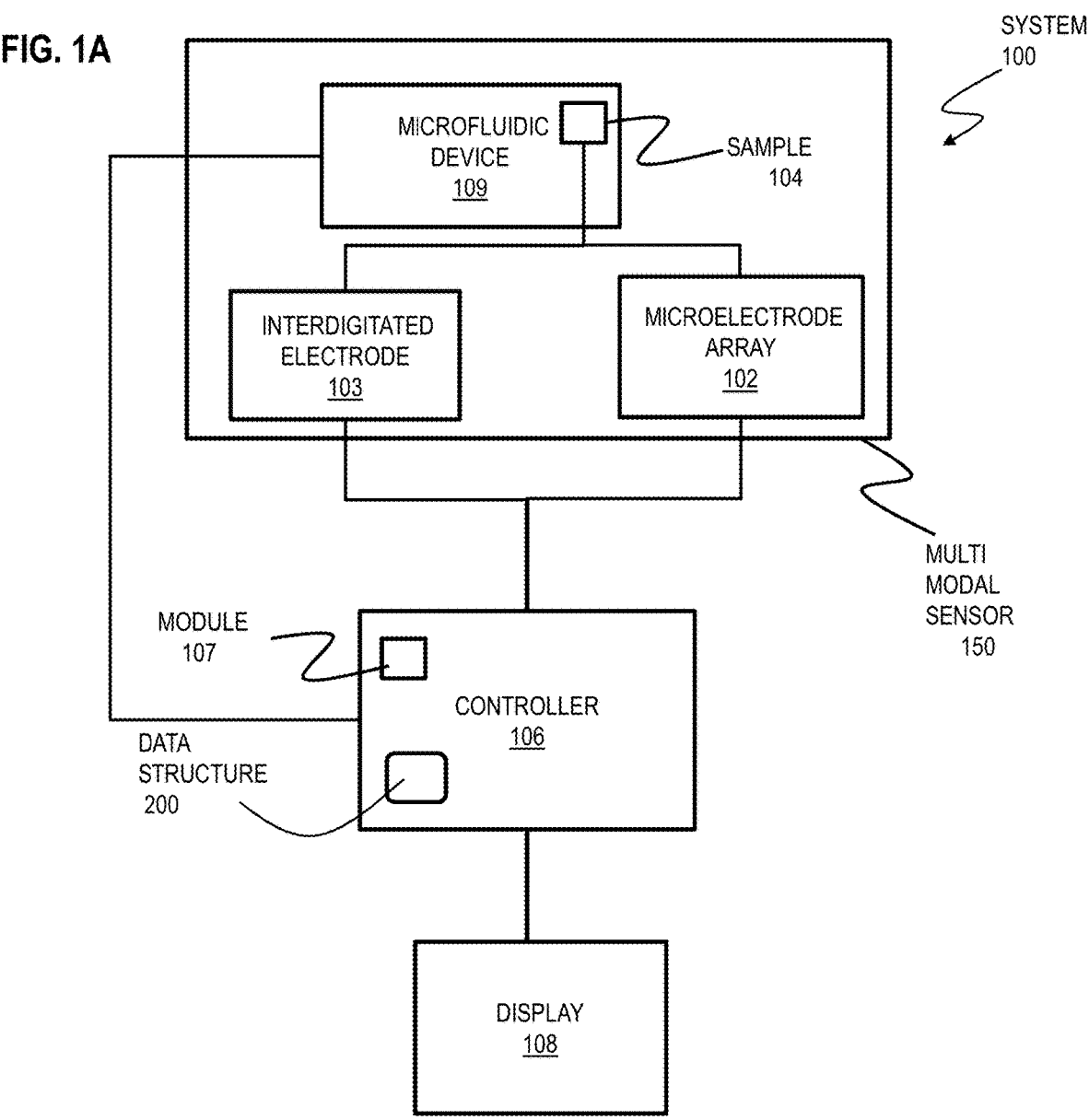
FIG. 1A is a block diagram that illustrates an example system for determining a presence of a microorganism in a sample, according to an embodiment.

It is here recognized that conventional methods have been developed to diagnose whether organisms are infected with a pathogenic microorganism. These conventional methods typically determine whether a test sample from the organism includes a pathogenic microorganism. One such conventional method relies on Polymerase Chain Reaction (PCR) that compares a Deoxyribonucleic acid (DNA) sequence of the test sample with the DNA sequence of a pathogenic microorganism (e.g. live bacteria).

It is also here recognized that conventional methods have been developed in the field of microbiology to determine a presence of a microorganism in a test sample. However, such conventional methods are inefficient as they require long time periods (e.g. hours, days) to provide results.

The inventors of the present invention recognized that conventional methods to determine a presence of a microorganism in a sample are particularly inefficient, including conventional methods that diagnose whether organisms are infected with pathogenic microorganisms. The inventors of the present invention recognized that early detection of the disease in the organism and assessment of overall organism health is a paramount unmet need of conventional diagnosing methods. Such early detection advantageously permits treatment to commence at earlier stage than in conventional methods. Specifically, the inventors of the present invention recognized that early detection of pathogenic microorganisms in plants (e.g. HLB in citrus trees) and assessment of overall plant health is an unmet need in certain plant industries.

The inventors of the present invention developed a method that addresses the above drawbacks of conventional methods, i.e. where long time periods are required to obtain results and pathogenic microorganisms are not easily distinguishable from non-pathogenic microorganisms and live bacteria are not easily distinguishable from dead bacteria. In one embodiment, the method stores a plurality of electrophysiological signatures and/or impedance signatures of a plurality of microorganisms in a database. In this embodiment, the method then generates an electrophysiological and/or impedance signature of a sample obtained from an organism and compares the electrophysiological and/or impedance signature of the sample with the plurality of electrophysiological and/or impedance signatures from the database. In this embodiment, the method then identifies a presence of one of the microorganisms in the sample, based on a correlation between the electrophysiological and/or impedance signature of the sample and a stored electrophysiological and/or impedance signature of one of the microorganisms. One advantage of this embodiment of the method is that the result (e.g. an identified presence of one of the microorganisms in the sample) is obtained on a much shorter time scale than conventional microbiology techniques.

A method and apparatus are described for determining a presence of a microorganism in a sample. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of the determining a presence of a microorganism in a sample. In one embodiment, the invention is described in the context of determining a presence of a pathogenic microorganism in a sample. In another embodiment, the invention is described in the context of determining a presence of fungi in a sample. In another embodiment, the invention is described in the context of determining a presence of viruses in a sample. In another embodiment, the invention is described in the context of determining a presence of bacteria in a sample. In another embodiment, the invention is described in the context of determining a presence of live bacteria or dead bacteria in a sample. In another embodiment, the invention is described in the context of determining a presence of a growth stage of bacteria in a sample. In another embodiment, the invention is described in the context of determining a presence of a replicating stage or non-replicating stage of bacteria in a sample. In another embodiment, the invention is described in the context of determining a treatment efficacy of a sample, i.e., presence of drug resistant bacteria or drug susceptible bacteria in the sample. In another embodiment, the invention is described in the context of determining a presence of a virus in a host cell. In another embodiment, the invention is described in the context of determining changes in electrical activity in a body fluid (e.g. serum, urine, sweat, saliva, sputum). In an embodiment, the electrical activity in the body fluid is determined as a screening method for treatment (e.g. TB).

As used herein the term "electrophysiological signature" refers to a value of one or more electrophysiological parameters of a potential signal received from an electrode (e.g. a microelectrode array (MEA)) during a time period that a sample is exposed to the electrode. In one embodiment, the electrophysiological parameter is an average peak amplitude of the action potential signal over the time period. In another embodiment, the electrophysiological parameter is a peak rate, defined as a number of peaks per second of the action potential signal over the time period. In another embodiment, the electrophysiological parameter is frequency defined as an inverse of a time gap between consecutive cycles of the action potential signal. In another embodiment, the electrophysiological parameter is burst activity defined as a group of cycles of the action potential signal. In another embodiment, the electrophysiological parameter is time between bursts defined as the time gap between consecutive cycles of the action potential signal.

As used herein the term "impedance signature" refers to a value of one or more parameters of an impedance signal received from an electrode (e.g. a microelectrode array (MEA) or interdigitated electrode (IDE)) during a time period that a sample is exposed to the electrode. In one embodiment, a first impedance signal is measured during the time period that the sample (including a microorganism) is exposed to the electrode and a second impedance signal is measured during the time period that a control sample (excluding the microorganism) is exposed to the electrode. In an embodiment, the parameters of the impedance signal in the impedance signature includes a difference in the value of the first impedance signal and the value of the second impedance signal including the value of one or more peak values in the difference. In other embodiments, the parameters of the impedance signal in the impedance signature include the value of the first impedance signal and/or the second impedance signal and/or the difference between the first and second impedance at time increments (e.g. 1 hour) over the time period. In other embodiments, the parameters of the impedance signal in the impedance signature include a peak value of the first impedance signal and/or the second impedance signal over the time period. In still other embodiments, the parameters of the impedance signal in the impedance signature includes a time value during the time period corresponding to one or more peak values of the first impedance signal and/or one or more peak values of the second impedance signal and/or one or more peak values in the difference between the first and second impedance value. In still other embodiments, the parameters of the impedance signal in the impedance signature is a slope of the impedance signal (e.g. value of a positive slope or a positive change in the slope) or a time value along the time period corresponding to the slope of the impedance signal. In still other embodiments, the parameters of the impedance signal in the impedance signature is a change in the slope of the impedance signal (e.g. one or more peak rates of change of the slope of the impedance signal over the time period or the time values corresponding to the one or more peak rates of change). In still other embodiments, the parameters of the impedance signal in the impedance signature is the frequency at which the impedance signal is measured.

As used herein the term "sample" refers to a biological specimen including, for example, blood, sputum, serum, sweat, saliva, tissue, urine, leaf extract, sap, etc. taken from an organism such as a plant, animal or human. In other embodiments, the term "sample" means a liquid culture or growth media solution or a Tryptic soy broth (TYB) or any enriched bacterial growth media.

As used herein the term "HLB" refers to a disease of citrus caused by a vector-transmitted pathogen. The causative agents are motile bacteria, *Candidatus Liberibacter* spp. The disease is vectored and transmitted by the Asian citrus psyllid, *Diaphorina citri*, and the African citrus psyllid, *Trioza erytreae*, also known as the two-spotted citrus psyllid. It has also been shown to be graft-transmissible. Three different types of HLB are currently known: The heat-tolerant Asian form, and the heat-sensitive African and American forms. The disease was first described in 1929 and first reported in China in 1943. The African variation was first reported in 1947 in South Africa, where it is still widespread. Eventually, it affected the United States, reaching Florida in 2005. Within three years, it had spread to the majority of citrus farms. The rapid increase in this disease has threatened the citrus industry not only in Florida, but the entire US. As of 2009, 33 countries have reported HLB infection in their citrus crop. HLB is distinguished by the common symptoms of yellowing of the veins and adjacent tissues; followed by splotchy mottling of the entire leaf, premature defoliation, dieback of twigs, decay of feeder rootlets and lateral roots, and decline in vigor, ultimately followed by the death of the entire plant. Affected trees have stunted growth, bear multiple off-season flowers (most of which fall off), and produce small, irregularly shaped fruit with a thick, pale peel that remains green at the bottom and tastes very bitter. Common symptoms can often be mistaken for nutrient deficiencies; however, the distinguishing factor between nutrient deficiencies is the pattern of symmetry. Nutrient deficiencies tend to be symmetrical along the leaf vein margin, while HLB has an asymmetrical yellowing around the vein. The most noticeable symptom of HLB is greening and stunting of the fruit, especially after ripening.

Periwinkle plants are easily infected with HLB and respond well when experimentally treated with antibiotics. Researchers are testing the effect of penicillin G sodium and biocide 2,2-dibromo-3-nitrilopropionamide as potential treatments for infected citrus plants based on the positive results that were observed when applied to infected periwinkle. No naturally immune citrus cultivars have been identified; however, creating genetically modified citrus may be a possible solution, but serious questions of its acceptability to consumers exist. A researcher at Texas AgriLife Research reported in 2012 that incorporating two genes from spinach into citrus trees improved resistance to citrus greening disease in greenhouse trials.

1. Overview

FIG. 1A is a block diagram that illustrates an example system 100 for determining a presence of a microorganism in a sample, according to an embodiment. The system 100 includes a microelectrode array (MEA) 102 with a plurality of electrodes through which neural signals are obtained or delivered, essentially serving as neural interfaces that connect neurons to electronic circuitry. In one embodiment, the MEA 102 is a non-implantable MEA, used in vitro. In other embodiments, the MEA 102 is an implantable MEA 102, used in vivo. In some embodiments, the MEA 102 is a grid of microelectrodes defined using traditional microfabrication and assembly processes with nanomaterials post-processed on the electrodes to improve the sensitivity of the electrode to capture signals from various microorganisms (e.g. pathogens).

As depicted in FIG. 1A, a sample 104 is obtained and exposed to the MEA 102 using a microfluidic device 109. In an embodiment, the microfluidic device 109 is used to manipulate or move or position the sample 104 so that it is exposed to the MEA 102. In one embodiment, the microfluidic device 109 includes one or more channels that are used to direct or position the sample 104 and one or more electrodes of the MEA 102 are aligned with the channel. In some embodiments, the microfluidic device 109 is excluded and the sample 104 is exposed to the MEA 102. The sample 104 is not part of the system 100. In one embodiment, the sample 104 includes a microorganism (e.g. bacteria, fungi, virus) obtained from an organism (e.g. plant, animal, etc). Neurons and muscle cells of the sample 104 create ion currents through their membranes, causing a change in voltage between the inside and the outside of the cell. This voltage is detected by electrodes of the MEA 102 as an action potential signal that is transmitted to the controller 106. In some embodiments, each electrode of the MEA 102 generates an action potential signal that is transmitted to the controller 106.

The controller 106 receives the action potential signal from the MEA 102 and generates an electrophysiological signature of the sample 104, based on the received action potential signal and/or receives the impedance signal from the IDE 103 and generates an impedance signature of the sample 104, based on the received impedance signal. The electrophysiological signature is a value of one or more electrophysiological parameters of the action potential signal over a time period. The impedance signature is a value of one or more parameters of the impedance signal over a time period. In one embodiment, the time period for the electrophysiological signature is about 100 milliseconds. In another embodiment, the time period for the impedance signature is in a range from about 8 hours to about 30 hours. In yet another embodiment, the frequency at which the impedance signal is measured is included in the impedance signature and extends within a range from about 0.1 Hz to about 10 MHz. In one embodiment, the electrophysiological parameter is an average peak value of the action potential signal. In another embodiment, the electrophysiological parameter is a peak rate, defined as a number of peaks per second. In an embodiment, the parameter of the impedance signature is one or more values (e.g. peak value) of the impedance signal or one or more values (e.g. peak value) of a difference between the impedance signal of the sample 104 (including the microorganism) and the impedance signal of a control sample 104 (excluding the microorganism).

During an initial storing phase of the system 100, after generating the electrophysiological and/or impedance signature of the sample 104, the controller 106 stores the electrophysiological and/or impedance signature in a memory of the controller 106. In one embodiment, the controller 106 stores the electrophysiological and/or impedance signature in a data structure 200 discussed in more detail below. This is repeated for multiple samples 104 so that electrophysiological and/or impedance signatures from a variety of microorganisms are stored in the memory. During the initial storing phase, the microorganism present in each sample 104 is known and one or more parameters of the microorganism (e.g. type, growth stage, replicating status, etc) are known and stored in the memory along with the electrophysiological and/or impedance signature.

After the initial storing phase, the electrophysiological and/or impedance signature of an unknown sample 104 (e.g. a sample 104 with an unknown microorganism presence) is generated by the controller 106 and compared with the stored electrophysiological and/or impedance signatures in the memory. Based on this comparison, a presence of a microorganism in the unknown sample 104 is identified by the controller 106.

In some embodiments, the controller 106 performs a step based on the identified presence of a microorganism in the unknown sample 104. In one embodiment, the step involves presenting data on a display 108 that indicates the presence of the microorganism in the sample 104. In other embodiments, the step involves presenting data on the display 108 that indicates a recommended treatment for a source of the sample 104, based on the identified presence of the microorganism in the sample 104.

Figure 6:
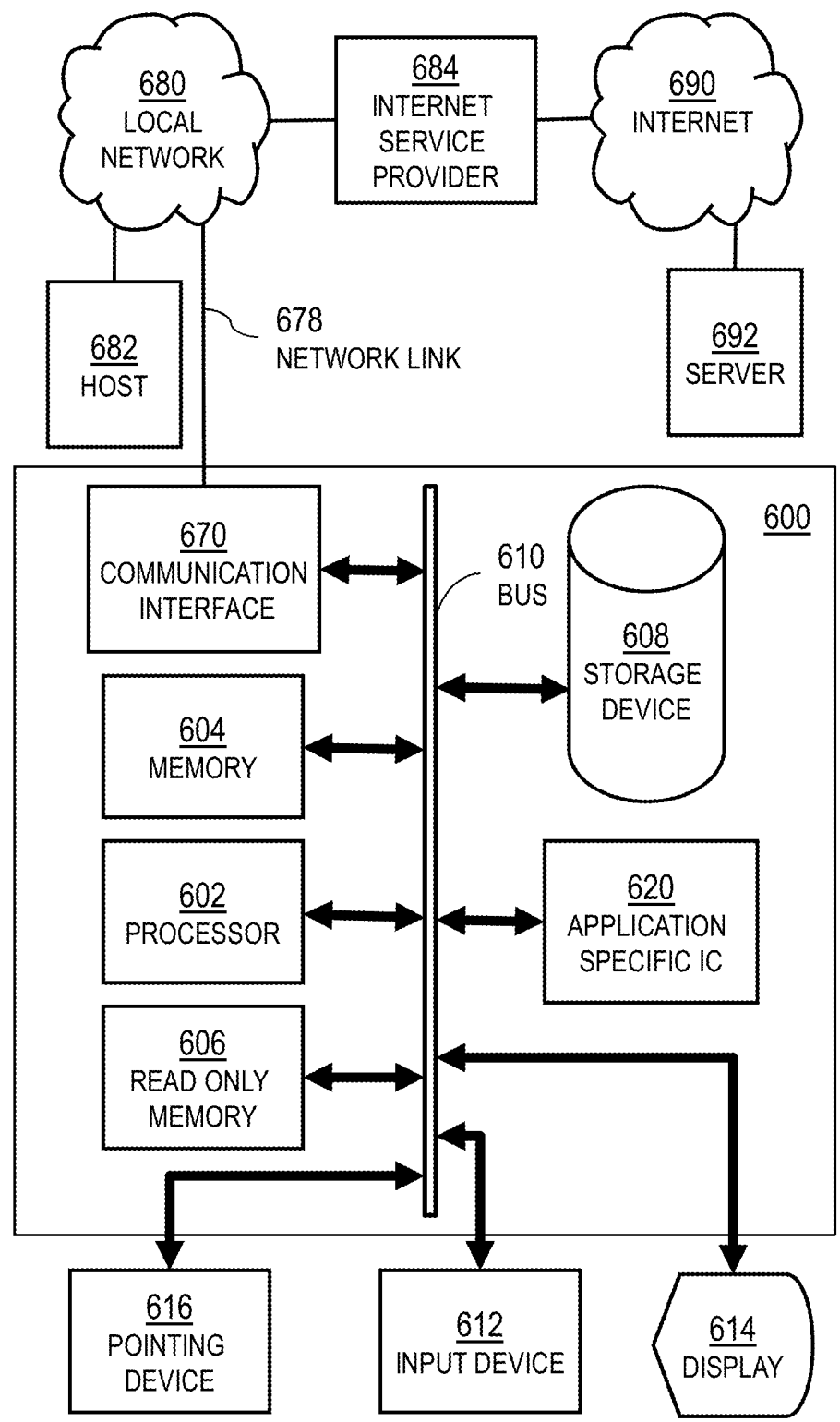
FIG. 6 is a block diagram that illustrates a computer system upon which an embodiment of the invention may be implemented.
Figure 7:
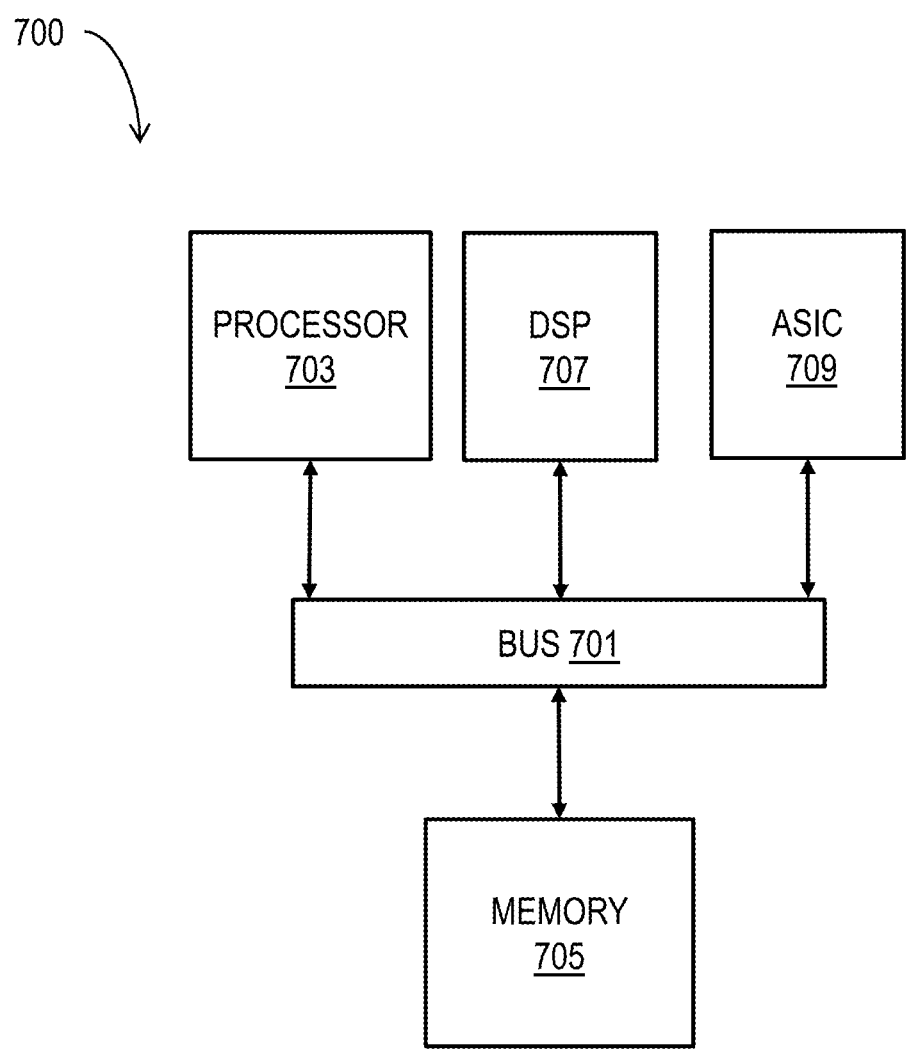
FIG. 7 is a block diagram that illustrates a chip set upon which an embodiment of the invention may be implemented.

The controller 106 includes a module 107 to perform one or more steps of a method described below with reference to FIG. 5A or a method described below with reference to FIG. 5B. In various embodiments, the controller 106 comprises one or more general purpose computer systems, as depicted in FIG. 6 or one or more chip sets as depicted in FIG. 7, and instructions to cause the computer or chip set to perform one or more steps of a method described below with reference to FIG. 5A or a method described below with reference to FIG. 5B.

In other embodiments, the system 100 can be used to determine a presence of a microorganism in a sample using parameters other than electrophysiological parameters. In these embodiments, the system 100 can be used to determine the presence of a microorganism in the sample using parameters other than parameters related to electrical activity of the sample. In one embodiment, the system 100 includes an interdigitated electrode (IDE) 103 that measures an impedance of the sample 104. In an embodiment, the microfluidic device 109 exposes the sample 104 to the IDE 103. In one example embodiment, the microfluidic device 109 includes one or more channels that are used to position or direct the sample 104 (e.g. liquid sample) and the IDE 103 includes one or more electrodes that are aligned with one or more channels of the microfluidic device 109. The parameter is capacitance of the sample, measured by the impedance between two electrodes of the IDE 103 that are activated with a potential signal at a range of frequencies. In an example embodiment, the capacitance is used to determine an area of the sample, and how the area of the sample changes over time. In an example embodiment, the capacitance of the sample is used to determine a presence of a virus in the sample. In an example embodiment, the capacitance of the sample is used to determine the presence of a virus in the sample, based on determining a change in area (e.g. viral replication) over time of the sample.

In other embodiments, the controller 106 receives signals other than the action potential from the MEA 102, such as an impedance signal from the IDE 103 indicating an impedance between electrodes of the IDE 103. In these embodiments, an impedance signature of the sample 104, based on a value of one or more parameters of the impedance signal is stored in the memory of the controller 106 as an impedance signature of the sample 104, in a similar manner as the electrophysiological signature is stored in the memory of the controller 106. In some embodiments of the system 100, the IDE 103 is excluded and only the electrophysiological signatures are stored in the memory of the controller 106. In other embodiments of the system 100, the MEA 102 is excluded and only the impedance signatures are stored in the memory of the controller 106. In yet other embodiments of the system 100, the MEA 102 and the IDE 103 are included and the electrophysiological signatures and the impedance signatures are stored in the memory of the controller 106. In some embodiments, the electrodes of the IDE 103 used to generate the impedance signal are different than the MEA 102. In one embodiment, a baseline group of cells engage the electrodes of the IDE 103 and the controller 106 activates the electrodes with a potential signal at a range of frequencies (e.g. 0.1 Hz to 100 MHz). The impedance between the electrodes of the IDE 103 is measured at each potential frequency and stored in a memory of the controller 106. In an embodiment, a sample 104 of cells engages the electrodes. As the cells of the sample 104 undergo one or more growth stages, the impedance between the electrodes of the IDE 103 is measured and compared with the stored impedance in the memory of the controller 106 to determine a presence of a virus or bacteria in the sample 104. In other embodiments, the IDE 103 measures the impedance of a control sample 104 in an absence of the microorganism and the impedance signal of the control sample 104 is used by the controller 106 to store the impedance signature (e.g. to calculate a difference between a value of the impedance signal of the sample 104 including the microorganism and a value of the impedance signal of the control sample 104) of the sample 104 including the microorganism.

In other embodiments, the controller 106 is communicatively coupled to the microfluidic device 109 such that the controller 106 can transmit one or more signals to the microfluidic device 109 or a device (e.g. injection device) that directs the sample 104 into the microfluidic device 109 to affect the positioning or manipulation of the sample 104 (e.g. liquid sample) relative to the MEA 102 and/or the IDE 103. In another embodiment, the controller 106 transmits a signal to a housing (e.g. incubator) where the microfluidic device 109 and the MEA 102 and/or IDE 103 are positioned, to control a temperature (e.g. 37C) of the housing and/or to rotate the housing (e.g. 150 rpm) to ensure that the microorganism in the sample 104 does not stagnate during the measurement by the MEA 102 and/or IDE 103.

Figure 1B:
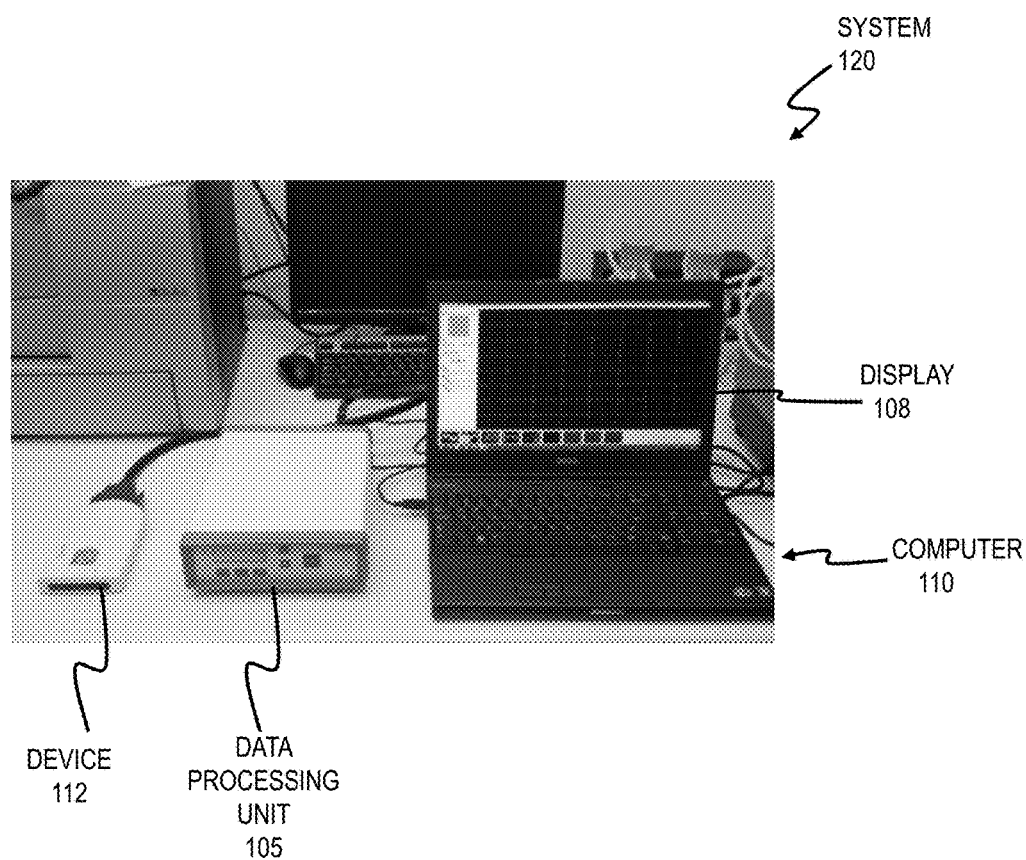
FIG. 1B is an image that illustrates an example system for determining a presence of a microorganism in a sample, according to an embodiment.

FIG. 1B is an image that illustrates an example system 120 for determining a presence of a microorganism in a sample, according to an embodiment. The system 120 includes a device 112 with a slot in which the microfluidic device 109 and the MEA 102 and/or IDE 103 are received after the sample 104 is positioned in the microfluidic device 109 and exposed to the MEA 102 and/or the IDE 103. In an example embodiment, the device 112 is a MUSE® MEA system manufactured by Axion BioSystems, Atlanta Ga. In another embodiment, the microfluidic device 109 and the MEA 102 and/or IDE 103 are received in the slot of the device 112 after multiple samples 104 are positioned in the microfluidic device 109. The device 112 transmits the action potential signal(s) from the MEA 102 and/or the impedance signal from the IDE 103 to a data processing unit 105. In some embodiments, the device 112 converts the action potential signal data and/or the impedance signal data from analog to digital form and amplifies the digitized information before transmitting the information to the data processing unit 105. The information is multiplexed by the data processing unit 105 and transmitted (e.g. via USB cable) to the computer 110. In some embodiments, the computer 110 includes the controller 106 of FIG. 1A and generates the electrophysiological signature and/or impedance signature based on the received data from the data processing unit 105. In an example embodiment, AXIS® electrophysiology software is run on the computer 110, written by Axion BioSystems, Atlanta Ga. As depicted in FIG. 1A, in some embodiments, the controller 106 internally performs the functions of the device 112 and data processing unit 105 and thus a separate device 112 and data processing unit 105 is not required.

FIG. 1C is an image that illustrates an example of an exploded view of a first chip 122 of a multi-modal biosensor 150 of the system 100 of FIG. 1A, according to an embodiment. FIG. 1D is an image that illustrates an example of a perspective view of the first chip 122 of FIG. 1C, according to an embodiment. In an embodiment, the biosensor 150 integrates multiple sensing modalities onto a microfluidic platform to enable acquisition of multi-parameter data (e.g. electrophysiological data and impedance data) from a variety of microorganisms (e.g. a variety of bacteria) to allow for rapid detection and identification of microorganisms in a sample.

Figures 1H, 1I, 1J, 1K:
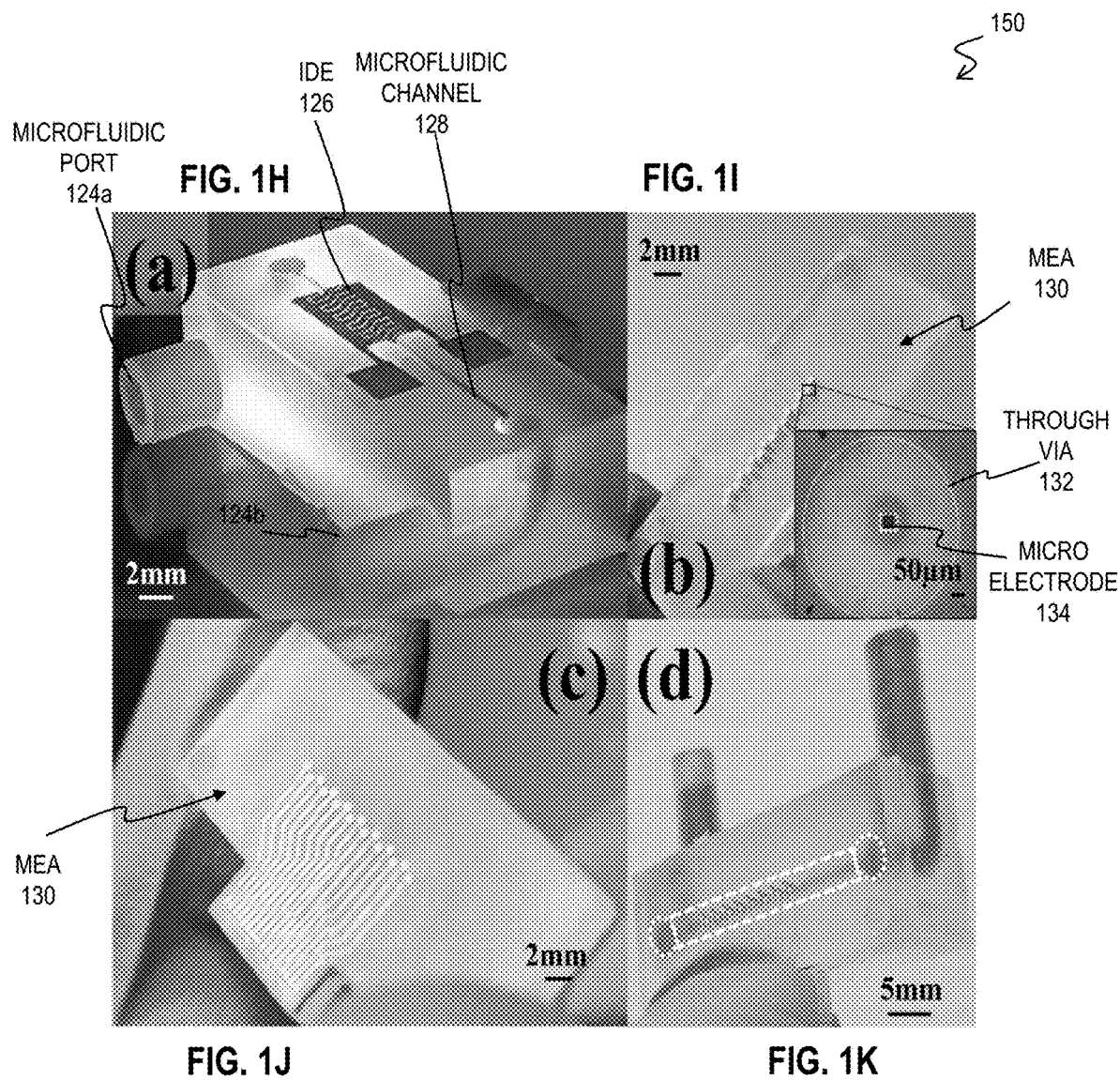
FIG. 1H is an image that illustrates an example of a top perspective view of an Interdigitated Electrode (IDE) aligned with a microfluidic channel in a first chip of a multi-modal biosensor of the system of FIG. 1A, according to an embodiment.
FIG. 1I is an image that illustrates an example of a top perspective view of a Microelectrode Array (MEA) in a second chip of a multi-modal biosensor of the system of FIG. 1A, according to an embodiment.
FIG. 1J is an image that illustrates an example of a bottom perspective view of the MEA in the second chip of FIG. 1I, according to an embodiment.
FIG. 1K is an image that illustrates an example of a multi-modal biosensor of the system of FIG. 1A, according to an embodiment.
Figure 1L:
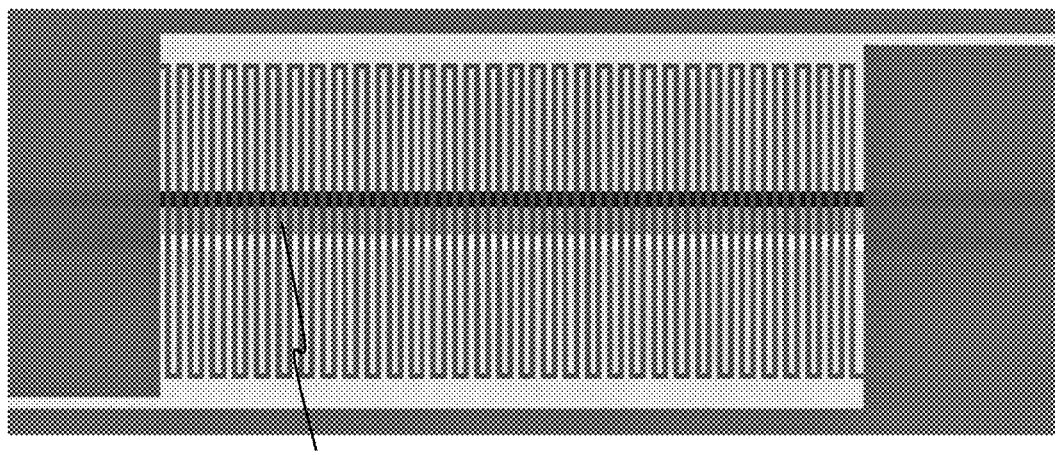
FIG. 1L is an image that illustrates an example of a top view of the IDE aligned with the microfluidic channel of FIG. 1H, according to an embodiment.
Figure 1M:
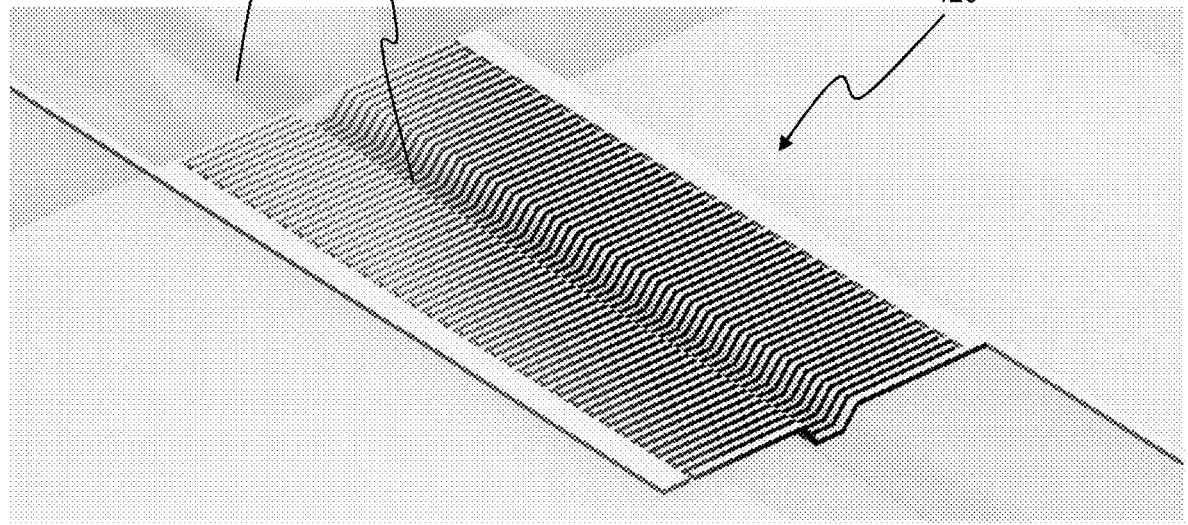
FIG. 1M is an image that illustrates an example of a perspective view of the IDE aligned with the microfluidic channel of FIG. 1H, according to an embodiment.
Figure 1N:
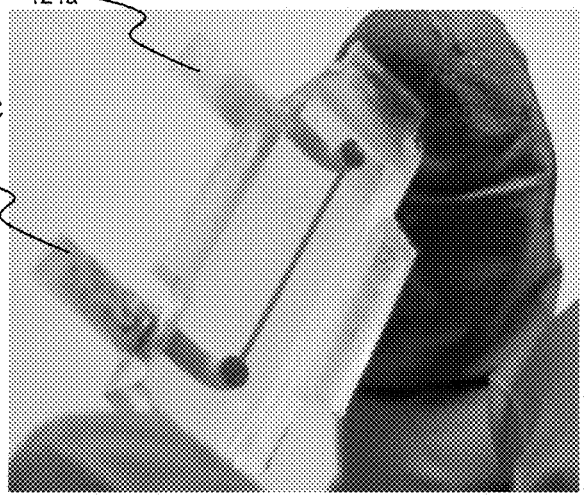
FIG. 1N is an image that illustrates an example of a perspective view of a liquid sample within the microfluidic channel of the multi-modal biosensor of FIG. 1H, according to an embodiment.

In an embodiment, the first chip 122 is a 3D printed chip that is made of proprietary photocurable resin material (from Form Labs Inc.) and has dimensions including a length of about 30 mm or in a range from about 20 mm to about 40 mm, a width of about 10 mm or in a range from about 5 mm to about 15 mm and a height of about 6 mm or in a range from about 2 mm to about 10 mm. The first chip 122 incorporates the microfluidic device 109 with a microfluidic channel 128. Although the microfluidic channel 128 depicted in FIG. 1C is linear, in other embodiments, the microfluidic channel 128 is non-linear (e.g. circular, arc shaped, square shaped, rectangular shaped, shaped according to any polygon, etc) along the surface of the first chip 122 and/or multiple microfluidic channels 128 are provided (e.g. a first channel 128 to position a sample 104 with a microorganism and a second channel 128 to position a control sample 104 excluding a microorganism) to advantageously provide for simultaneous gathering of impedance and/or electrophysiological data from the samples within the multiple channels 128. In one embodiment, the microfluidic channel 128 has a length of about 20 millimeters (mm) or in a range from about 15 mm to about 25 mm, a width of about 300 µm or in a range from about 250 µm to about 350 µm and a depth of about 100 µm or in a range from about 50 µm to about 150 µm. The microfluidic device 109 incorporated in the first chip 122 also includes a pair of microfluidic ports 124a, 124b which serve as respective entry and exit ports to the microfluidic channel 128. In some embodiments, the ports 124a, 124b are coupled to an injection mechanism to provide a dynamic flow of the sample 104 along the microfluidic channel 128 over a time period (e.g. 24 hours to 96 hours). In other embodiments, the sample 104 is directed into the ports 124a, 124b and the microfluidic channel 128 after which the ports 124a, 124b are sealed to provide a static arrangement of the sample 104 relative to the ports 124a, 124b. FIG. 1K is an image that illustrates an example of the sample 104 within the microfluidic channel 128 and sealed ports 124a, 124b, according to an embodiment. FIG. 1N is an image that illustrates an example of a perspective view of a liquid sample 104 within the microfluidic channel 128 of the multi-modal biosensor 150 with sealed ports 124a, 124b, according to an embodiment. In an example embodiment, to mobilize the sample 104 within the microfluidic channel 128 in the static arrangement during the impedance measurements, the biosensor 150 is continuously mobilized (e.g. rotated in an incubator at a specific rotation speed), to prevent the sample 104 and/or the microorganism within the sample 104 from stagnating.

An IDE 126 is also provided in the biosensor 150 to provide impedance measurements of the sample 104. In one embodiment, the IDE 126 has a width of about 400 µm or in a range from about 300 µm to about 500 µm and a gap between adjacent electrodes of about 15 µm or in a range from about 5 µm to about 20 µm. In an embodiment, the IDE 126 is defined by e-beam evaporation of Ti/Au using a shadow mask 127 and a direct laser etch to create IDE fingers. FIG. 1L is an image that illustrates an example of a top view of the IDE 126 (with the IDE fingers formed by the direct laser etching) aligned with the microfluidic channel 128 of the biosensor 150, according to an embodiment. FIG. 1M is an image that illustrates an example of a perspective view of the IDE 126 aligned with the microfluidic channel 128 of the biosensor 150, according to an embodiment. In an embodiment, the IDE 126 detects impedance data of the sample 104 positioned along the length of the microfluidic channel 128 and the impedance data is transmitted to the controller 106 (not shown in FIGS. 1C-1D) where the controller 106 stores the impedance signature based on the impedance data and/or compares the impedance signature of the sample 104 with the stored impedance signatures in the memory of the controller 106. In an embodiment, the IDE 126 measures the impedance data of bacteria within the sample 104 to measure morphological changes of the bacteria.

FIG. 1E is an image that illustrates an example of through vias 132 formed in a second chip 123 of a multi-modal biosensor 150 of the system 100 of FIG. 1A, according to an embodiment. In an embodiment, the second chip 123 is made of proprietary photocurable resin material (from Form Labs Inc.) and has dimensions including a length of about 30 mm or in a range from about 20 mm to about 40 mm, a width of about 10 mm or in a range from about 5 mm to about 15 mm and a height of about 1.5 mm or in a range from about 0.5 mm to about 3 mm. In an embodiment, traces are screen printed on the second chip 123 using conductive ink. In an example embodiment, the through vias 132 have a diameter of about 400 µm or in a range from about 300 µm to about 500 µm. The through vias 132 are provided to form the MEA 102 in the biosensor 150.

FIG. 1F is an image that illustrates an example of microelectrodes 134 in the second chip 123 of a multi-modal biosensor 150 of the system 100 of FIG. 1A, according to an embodiment. In an embodiment, the microelectrodes 134 are defined by laser micromachining of a laminate 136 (e.g. biocompatible laminate). In one embodiment, the microelectrodes 134 have dimensions of about 30 µm×30 µm. The microelectrodes 134 are defined in the through vias 132 to form the MEA 102 in the biosensor 150.

FIG. 1G is an image that illustrates an example of the first chip 122 of FIG. 1D laminated to the second chip 123 of FIG. 1F, according to an embodiment to form the biosensor 150. In an embodiment, two chips 122, 123 are bonded together using a biocompatible adhesive to form a bonded device 140.

FIG. 1H is an image that illustrates an example of a top perspective view of the IDE 126 aligned with the microfluidic channel 128 in the first chip 122 of the multi-modal biosensor 150 of the system 100 of FIG. 1A, according to an embodiment. In an embodiment, FIG. 1H depicts that the IDE 126 extends along a portion of the microfluidic channel 128 so that the IDE 126 can measure impedance data of the sample 104 positioned along the portion of the microfluidic channel 128.

FIG. 1I is an image that illustrates an example of a top perspective view of the MEA 130 in the second chip 123 of the multi-modal biosensor 150 of the system 100 of FIG. 1A, according to an embodiment. In an embodiment, the MEA 130 is formed by the microelectrode 134 that is defined in the through vias 132 of the second chip 123. FIG. 1I depicts the top surface of the second chip 123 and thus depicts the surface of the second chip 123 facing away from the microfluidic channel 128 when the second chip 123 is laminated and bonded to the first chip 122. In an embodiment, the through vias 132 and microelectrodes 134 are formed on the second chip 123 so to be aligned with the microfluidic channel 128 when the chips 122, 123 are laminated and bonded together. In an embodiment, the IDE 126 is positioned along a first side (e.g. bottom side) of the microfluidic channel 128 and the MEA microelectrodes 134 are positioned along a second side opposite to the first side (e.g. top side) of the microfluidic channel 128 when the chips 122, 123 are laminated and bonded together.

FIG. 1J is an image that illustrates an example of a bottom perspective view of the MEA 130 in the second chip 123 of FIG. 1I, according to an embodiment. The traces along the second chip 123 are depicted that are printed along the surface of the second chip 123 using conductive ink. In an embodiment, the second chip 123 includes a plurality of traces that are arranged based on the orientation of the microfluidic channel 128. In one embodiment, the number of traces is selected within a range from about 16 traces to about 64 traces. In some embodiments, the traces are positioned in one or more linear rows (e.g. 1 row of 16 traces, 2 rows of 8 traces, 2 rows of 32 traces, etc) where each linear row is aligned with the microfluidic channel 128 when the chips 122, 123 are bonded. In an embodiment, the microelectrodes 134 of the MEA 130 are electrically connected to the controller 106 (not shown in FIG. 1J) so that the controller 106 receives the action potential signal from the MEA 130 and stores the electrophysiological signature of the sample 104 in the memory of the controller 106.

Figure 1O:
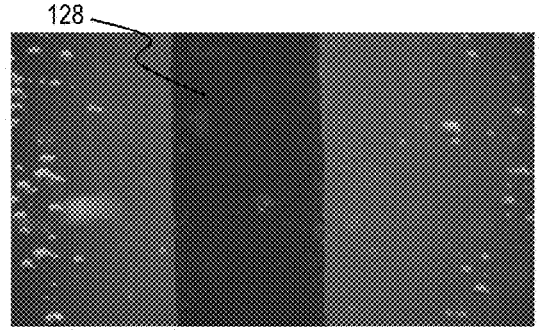
FIGS. 1O-1R are images that illustrate an example of a top view of the liquid sample contained within the microfluidic channel of FIG. 1H at various time stages, according to an embodiment.
Figure 1P:
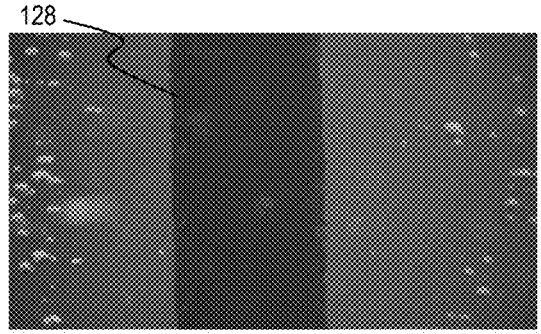
Figure 1Q:
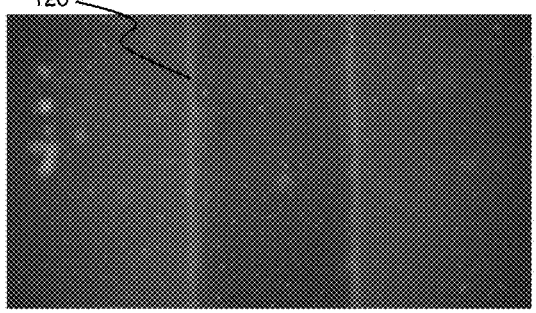
Figure 1R:
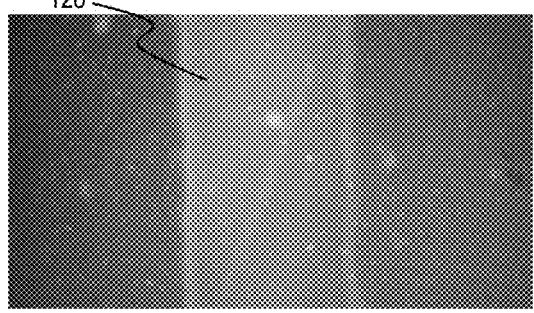

FIG. 1K is an image that illustrates an example of the microfluidic channel 128 of FIG. 1H, according to an embodiment. In an embodiment, the sample 104 within the microfluidic channel 128 is bacterial growth media (e.g. Tyrptic soy broth). The bacterial growth media sample 104 is advantageous since in one embodiment it includes a florescent dye (e.g. R6G) which emits florescence and thus clearly indicates if the liquid sample 104 deviates from the microfluidic channel 128 (e.g. indicates whether there is an undesired leak in the bond between the chips 122, 123). FIGS. 1O-1R are images that illustrate an example of a top view of the liquid sample 104 (e.g. including R6G) contained within the microfluidic channel 128 of FIG. 1H at various time stages, according to an embodiment. FIG. 1O depicts that the liquid sample 104 is contained within the microfluidic channel 128 (no leaks) after about 0 hours within the microfluidic channel 128. FIG. 1P depicts that the liquid sample 104 is contained within the microfluidic channel 128 (no leaks) after about 24 hours within the microfluidic channel 128. FIG. 1Q depicts that the liquid sample 104 is contained within the microfluidic channel 128 (no leaks) after about 48 hours within the microfluidic channel 128. FIG. 1R depicts that the liquid sample 104 is contained within the microfluidic channel 128 (no leaks) after about 72 hours within the microfluidic channel 128.

Figures 2A, 2B, 2C, 2D:
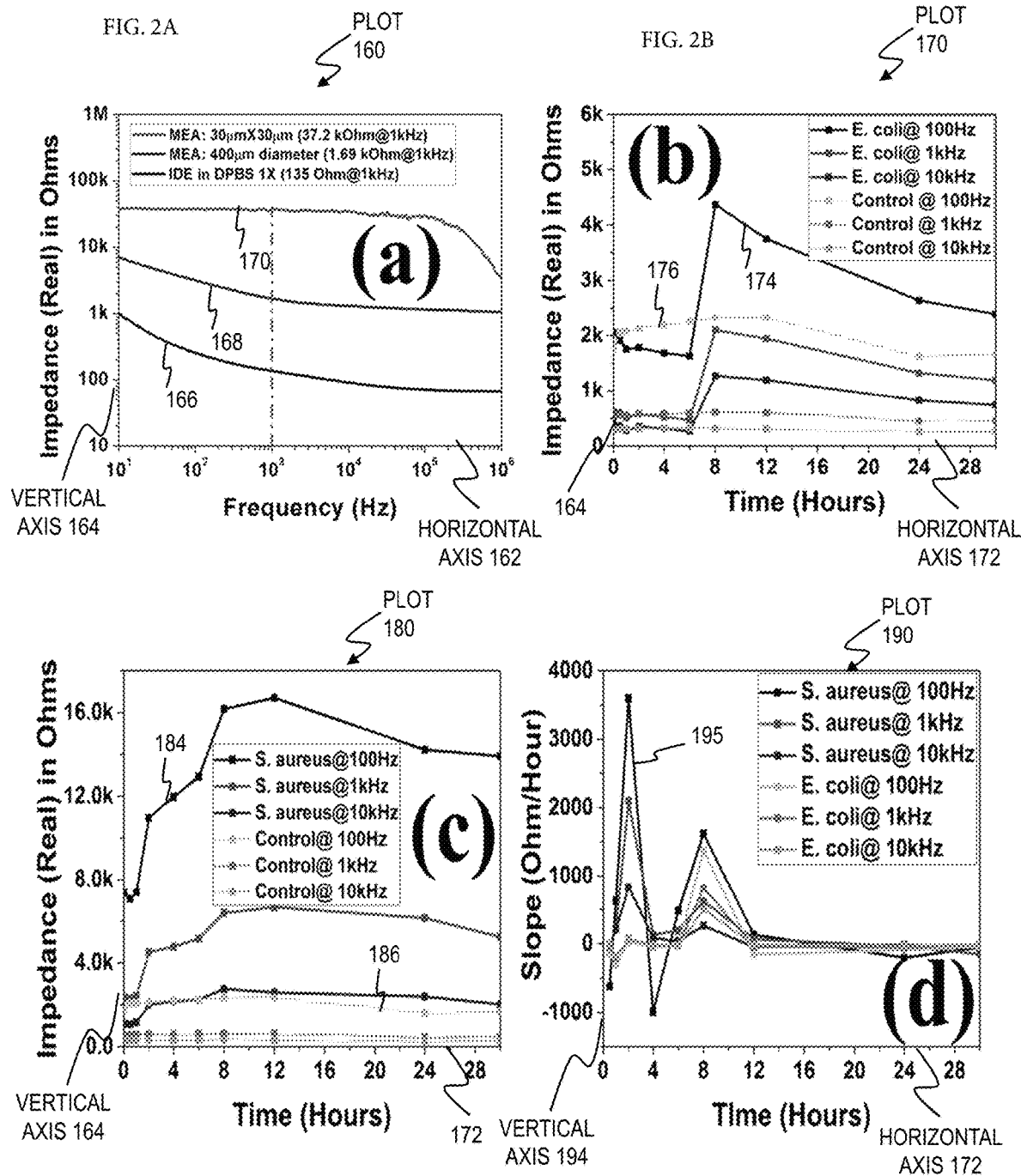
FIG. 2A is an image that illustrates an example of traces of full spectrum impedance measured by the IDE and various sized MEAs of the system of FIG. 1A without a sample, according to an embodiment.
FIG. 2B is an image that illustrates an example of traces of impedance of *Escherichia coli* measured by the IDE of the system of FIG. 1A, according to an embodiment.
FIG. 2C is an image that illustrates an example of traces of impedance of *Staphylococcus aureus* measured by the IDE of the system of FIG. 1J, according to an embodiment.
FIG. 2D is an image that illustrates an example of a trace of slope of the impedance trace of FIG. 2C, according to an embodiment.

FIG. 2A is an image that illustrates an example of a plot 160 including traces of impedance or a full spectrum impedance measured by the IDE 126 and various sized MEAs 130 of the system 100 of FIG. 1A without a sample, according to an embodiment. The horizontal axis 162 is frequency in units of Hertz (Hz). The vertical axis 164 is impedance in units of Ohms. A first trace 166 depicts the impedance measured by the IDE 126 in the microfluidic channel 128 in an absence of a sample 104 or in presence of a control sample 104 (e.g. without a microorganism) over a range of frequency. A second trace 168 depicts the impedance measured by the MEA 130 (e.g. 400 μm diameter) in the microfluidic channel 128 in an absence of a sample 104 or presence of a control sample 104 over a range of frequency. A third trace 170 depicts the impedance measured by the microelectrodes 134 of the MEA 130 (e.g. 30 μm×30 μm) in the microfluidic channel 128 in an absence of a sample 104 or presence of a control sample 104 over a range of frequency. In one embodiment, the traces 166, 168, 170 were generated using a control sample 104 (e.g. bacterial growth media such as tryptic soy broth (TSB)) without any microorganism present in the sample 104. As depicted in the plot 160, the measured impedance of the traces 166, 168, 170 varies with a size of the measuring electrode. In an embodiment, the trace 170 indicates that the impedance measured by the microelectrodes 134 is about 37.2 kΩ @ 1 kHz and is comparable to the impedance measured by the conventional MEA (e.g. 30 μm diameter).

FIG. 2B is an image that illustrates an example of a plot 170 that shows traces 174, 176 of impedance of *Escherichia coli* measured by the IDE 126 of the system 100 of FIG. 1A, according to an embodiment. The horizontal axis 172 is time in units of hours. The trace 174 is the measured impedance of the sample 104 at 100 Hz (e.g. bacterial growth media with *Escherichia coli*) in the microfluidic channel 128 using the IDE 126. The trace 176 is the measured impedance of a control sample 104 at 100 Hz (e.g. bacterial growth media without *Escherichia coli*). Other traces are also depicted for the measured impedance of the sample 104 and control sample 104 at 1 kHz and 10 kHz using the IDE 126. In an embodiment, the impedance is measured at regular time increments (e.g. 1 hour) over a time period (e.g. 28 hours). In another embodiment, the impedance of the sample 104 (with microorganism) and the impedance of the control sample 104 (without microorganism) is measured at multiple frequencies at each time increment (e.g. 100 Hz, 1 KHz, 10 KHz). In an embodiment, the impedance data is transmitted from the IDE 126 to the controller 106 and the controller 106 stores the impedance signature in the memory based on one or more parameter values of the impedance data. A difference in the value of the impedance of the sample 104 (e.g. trace 174) and the value of the impedance of the control sample 104 (e.g. trace 176) is calculated by the controller 106 and stored in the memory of the controller 106 as the impedance signature for the microorganism. In an example embodiment, a difference in the value of the impedance values in the trace 174 and the value of the impedance values in the trace 176 are calculated by the controller 106 and stored in the memory of the controller 106 as an impedance signature for *Escherichia coli*. In other embodiments, the controller 106 stores one or more values of the trace 174 and/or one or more peak values of the trace 174 and/or one or more time values (e.g. 2 hours or 8 hours in FIG. 2B) along the axis 172 corresponding to one or more peak values in the memory as the impedance signature for *Escherichia coli*. In some embodiments, the controller 106 determines the frequency at which the value of the difference in the value of the impedance of the sample 104 and the value of the impedance of the control sample 104 is maximum and stores this maximum value of the difference in the memory as the impedance signature (e.g. value of the difference in the trace 174 and trace 176 in FIG. 2B).

FIG. 2C is an image that illustrates an example of a plot 180 that shows traces 184, 186 of impedance of *Staphylococcus aureus* measured by the IDE 126 of the system 100 of FIG. 1A, according to an embodiment. The horizontal axis 172 is time in units of hours. The trace 184 is the measured impedance of the sample 104 at 100 Hz (e.g. bacterial growth media with *Staphylococcus aureus*) in the microfluidic channel 128 using the IDE 126. The trace 186 is the measured impedance of a control sample 104 at 100 Hz (e.g. bacterial growth media without *Staphylococcus aureus*). Other traces are also depicted for the measured impedance of the sample 104 and control sample 104 at 1 kHz and 10 kHz using the IDE 126. In an embodiment, the impedance is measured at regular time increments (e.g. 1 hour) over a time period (e.g. 28 hours). The impedance signature of the impedance data of the traces in FIG. 2C is stored in a similar manner as above with respect to FIG. 2B. In an example embodiment, a difference in the value of the impedance values in the trace 184 and the value of the impedance values in the trace 186 are calculated by the controller 106 and stored in the memory of the controller 106 as an impedance signature for *Staphylococcus aureus*. In other embodiments, the controller 106 stores one or more values of the trace 184 and/or one or more peak values of the trace 184 and/or one or more time values (e.g. 2 hours or 8 hours in FIG. 2C) along the axis 172 corresponding to one or more peak values in the memory as the impedance signature for *Staphylococcus aureus*. In some embodiments, the controller 106 determines the frequency at which the value of the difference in the value of the impedance of the sample 104 and the value of the impedance of the control sample 104 is maximum and stores this value of the difference in the memory as the impedance signature (e.g. value of the difference in the trace 184 and trace 186 in FIG. 2B). In some embodiments, the controller 106 receives impedance data from the IDE 126 for other samples 104 and stores the impedance data as the impedance signature in a similar manner as discussed above with respect to FIGS. 2B-2C.

FIG. 2D is an image that illustrates an example of a plot 190 that shows a trace 195 of slope of the impedance trace 184 of FIG. 2C, according to an embodiment. In some embodiments, the controller 106 generates a trace 195 of a slope of the impedance curve 184 after receiving the impedance data from the IDE 126 over the time period. In an embodiment, the controller 106 determines one or more peak values of the trace 195 (e.g. at 2 hours or 8 hours) and/or one or more positive slope regions (e.g. between 0-2 hours or between 4-8 hours) of the trace 195 and stores these peak values and/or time regions as the impedance signature of the microorganism (e.g. *Staphylococcus aureus*) in the memory of the controller 106. In another embodiment, the controller 106 identifies one or more growth stages based on the values of the peak values of the trace 195 and/or the positive slope regions of the trace 195. In an example embodiment, the controller 106 determines that a first peak value (e.g. 2 hours in FIG. 2D) corresponds to an initiation of bacterial replication for the bacteria (e.g. *Staphylococcus aureus*). In yet another embodiment, the controller 106 determines that the second peak value (e.g. 8 hours in FIG. 2D) corresponds to growth kinetics of the bacteria (e.g. *Staphylococcus aureus*) that alters both the double layer capacitance and the resistance of the media before becoming asymptotic. In some embodiments, the biosensor 150 can be used to measure impedance data for a time period up to about 96 hours using the sample 104 (e.g. bacterial growth media).

Figure 3:
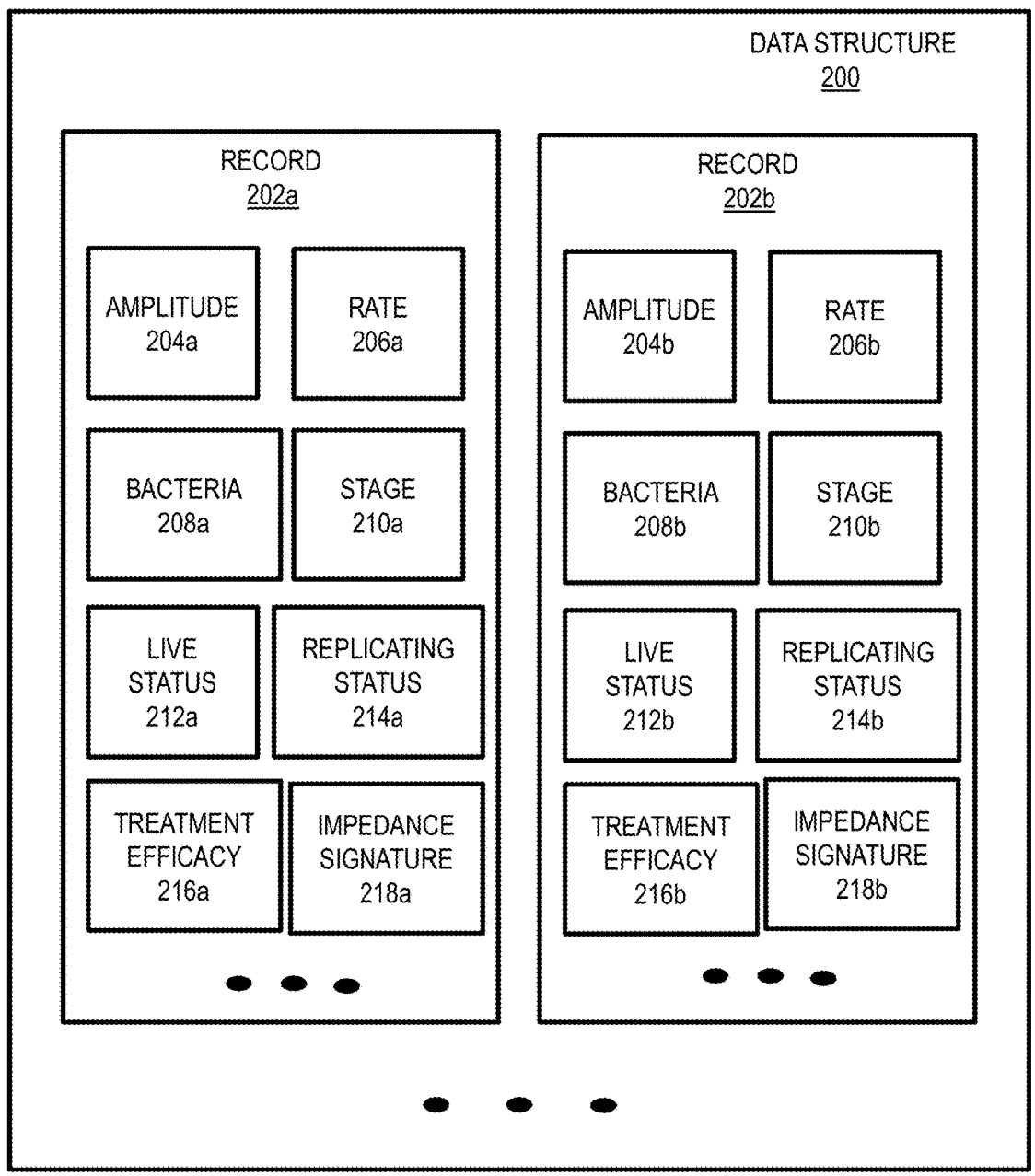
FIG. 3 is a block diagram that illustrates an example of a data structure for storing an electrophysiological and impedance signatures of a microorganism, according to an embodiment.

FIG. 3 is a block diagram that illustrates an example of a data structure 200 in a memory of the controller 106 for storing an electrophysiological signature of a microorganism during the initial storing phase and/or storing an impedance signature of a microorganism during the initial storing phase and/or storing an optical signature of a microorganism during the initial storing phase, according to an embodiment. In other embodiments, the controller 106 stores the electrophysiological signatures and/or impedance signatures in the memory of the controller 106, without the data structure 200. The electrophysiological signature and/or impedance signature is generated from the sample 104. In some embodiments, one or more parameters of the microorganism present in the sample 104 is known, such as the type of microorganism, a growth stage of the microorganism, etc. The data structure 200 resides on a computer-readable medium, such as a memory of the controller 106. In some embodiments, multiple data structures 200 are provided in the memory of the controller 106, where a first data structure 200 is used to store a first classification of microorganism (e.g. bacteria) and a second data structure 200 is used to store a second classification of microorganism (e.g. fungi, viruses, etc).

The data structure 200 includes multiple records 202, where a respective record 202 is used to store the electrophysiological signature and/or impedance signature of a respective sample 104 during the initial storing phase. In an example embodiment, the electrophysiological signature and/or impedance signature of a first sample 104 is stored in a first record 202a and the electrophysiological signature and/or impedance signature of a second sample 104 is stored in a second record 202b.

In some embodiments, each record 202a,b includes multiple fields including a first field 204a,b for holding data indicating a value of a first electrophysiological parameter (e.g. average peak amplitude) and a second field 206a,b for holding data indicating a value of a second electrophysiological parameter (e.g. peak rate) of the electrophysiological signature. Although FIG. 3 depicts two fields 204a,b 206a,b that hold data indicating the values of two electrophysiological parameters of the electrophysiological signature, more than two fields can be used to hold data indicating values of more than two electrophysiological parameters of the electrophysiological signature.

In some embodiments, each record 202a,b also includes additional fields for holding data indicating one or more known parameters of the microorganism present in the sample 104. In one embodiment, a third field 208a,b is provided for holding data indicating an identity of the microorganism present in the sample 104 (e.g. *Liberibacter crescens, Pseudomonas aeruginosa, Clavibacter michiganensis, Candidatus Liberibacter* spp, *Escherichia coli, Staphylococcus aureus*). In other embodiments, each record 202 includes a fourth field 210a,b for holding data indicating a growth stage of the microorganism present in the sample 104 (e.g. lag stage, exponential phase, stationary phase). In some embodiments, the controller 106 determines the growth stage of the microorganism based on the impedance data received from the IDE 126 and stores this determined growth stage in the fourth field 210a,b.

In still other embodiments, each record 202a,b includes a fifth field 212a,b for holding data indicating a live status of the microorganism present in the sample 104 (e.g. alive or dead). In an example embodiment, the fifth field 212a,b data is binary data (e.g. 0 for dead, 1 for alive or vice versa). For purposes of this description, "alive" means that the electrophysiological signature of the microorganism indicates at least a minimum threshold of electrical activity. For purposes of this description, "dead" means that the electrophysiological signature of the microorganism indicates no electrical activity or a degree of electrical activity that is less than the above minimum threshold.

In still other embodiments, each record 202a,b includes a sixth field 214a,b for holding data indicating a replicating status of the microorganism present in the sample 104 (e.g. replicating or non-replicating). In some embodiments, the sixth field 214a,b data is based on the fourth stage 210a,b data (e.g. growth stage). In one embodiment, the sixth field 214a,b data indicates a replicating status if the microorganism is in the exponential growth stage, i.e. fourth stage 210a,b data indicates the exponential growth stage. In another embodiment, the sixth field 214a,b data indicates a non-replicating status if the microorganism is in a growth stage other than the exponential growth stage, i.e. fourth stage 210a,b data indicates a growth stage other than the exponential growth stage. In some embodiments, the controller 106 determines the replicating status of the microorganism based on the impedance data received from the IDE 126 and stores this determined replicating status in the sixth field 214a,b.

In still other embodiments, each record 202a,b includes a seventh field 216a,b for holding data indicating a treatment efficacy of the microorganism present in the sample 104 (e.g. drug resistant or drug susceptible). In some embodiments, after recording the electrophysiological signature (e.g. first stage 204a,b and second stage 206a,b data) and/or the impedance signature (e.g. eighth field 218a,b data) in the data structure 200, the sample 104 is treated with a certain treatment (e.g. antibiotic). A subsequent post-treatment electrophysiological signature and/or impedance signature of the sample 104 is then generated and compared with the pre-treatment electrophysiological signature and/or impedance signature stored in the database 200. If the subsequent post-treatment electrophysiological signature and/or impedance signature demonstrates a threshold reduction in the presence of the microorganism in the sample 104, a positive treatment efficacy (e.g. drug susceptible) is stored in the seventh field 216a,b data. If the subsequent post-treatment electrophysiological signature and/or impedance signature does not demonstrate the threshold reduction in the presence of the microorganism in the sample 104, a negative treatment efficacy (e.g. drug resistant) is stored in the seventh field 216a,b data. Although FIG. 2 depicts one field 216a,b for storing treatment efficacy data for a single treatment, the data structure 200 can include multiple fields for storing treatment efficacy data for multiple treatments.

In still other embodiments, each record 202a,b includes an eighth field 218a,b for holding data indicating the impedance signature of the sample 104. In an embodiment, the eighth field 218a,b is for holding data indicating a value of a parameter of one or more impedance signals received by the controller 106 from the IDE 126. In an embodiment, the eighth field 218a,b is for holding data indicating a value of a parameter of the impedance signal from the IDE 126 measuring an impedance of the sample 104 including the microorganism. In another embodiment, the eighth field 218a,b is for holding data indicating a value of a parameter of the impedance signal from the IDE 126 measuring an impedance of the control sample 104 excluding the microorganism. In yet another embodiment, the eighth field 218a,b is for holding data indicating a difference in the value of the parameter of the impedance measured of the sample 104 including the microorganism and the values of the parameter of the impedance measured of the control sample excluding the microorganism. In yet further embodiments, the eighth field 218a,b is for holding data indicating a time value over the time period for any of the stored impedance data and/or a frequency at which the IDE 126 measured the stored impedance data.

In still other embodiments, each record 202 includes a fifth field 212 for holding data indicating a live status of the microorganism present in the sample 104 (e.g. alive or dead). In an example embodiment, the fifth field 212 data is binary data (e.g. 0 for dead, 1 for alive or vice versa). For purposes of this description, "alive" means that the electrophysiological signature of the microorganism indicates at least a minimum threshold of electrical activity. For purposes of this description, "dead" means that the electrophysiological signature of the microorganism indicates no electrical activity or a degree of electrical activity that is less than the above minimum threshold.

In still other embodiments, each record 202 includes a sixth field 214 for holding data indicating a replicating status of the microorganism present in the sample 104 (e.g. replicating or non-replicating). In some embodiments, the sixth field 214 data is based on the fourth stage 210 data (e.g. growth stage). In one embodiment, the sixth field 214 data indicates a replicating status if the microorganism is in the exponential growth stage, i.e. fourth stage 210 data indicates the exponential growth stage. In another embodiment, the sixth field 214 data indicates a non-replicating status if the microorganism is in a growth stage other than the exponential growth stage, i.e. fourth stage 210 data indicates a growth stage other than the exponential growth stage. In some embodiments, the controller 106 determines the replicating status of the microorganism based on the impedance data received from the IDE 126 and stores this determined replicating status in the sixth field 214.

In still other embodiments, each record 202 includes a seventh field 216 for holding data indicating a treatment efficacy of the microorganism present in the sample 104 (e.g. drug resistant or drug susceptible). In some embodiments, after recording the electrophysiological signature (e.g. first stage 204 and second stage 206 data) and/or the Although processes, equipment, and data structures are depicted in FIG. 1A and FIG. 1B as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

Although data structures, messages and fields are depicted in FIG. 3, as integral blocks in a particular order for purposes of illustration, in other embodiments, one or more data structures or messages or fields, or portions thereof, are arranged in a different order, in the same or different number of data structures or databases in one or more hosts or messages, or are omitted, or one or more additional fields are included, or the data structures and messages are changed in some combination of ways.

FIG. 4A is an image that illustrates plot 300 showing an example of traces 306 of a potential signal from the MEA 102 in FIG. 1A for different microorganism samples, according to an embodiment. Such traces of potential signals of different microorganism samples generated from a MEA are discussed in Masi E, Ciszak M, Santopolo L, Frascella A, Giovannetti L, Marchi E, Viti C, Mancuso S. 2015 *Electrical spiking in bacterial biofilms*, J. R. Soc. Interface 12: 20141036, which is incorporated by reference herein. The horizontal axis 302 is time in units of milliseconds (ms). The vertical axis 304 is potential amplitude in units of microvolts (μV). The first trace 306a is the action potential signal generated by the MEA 102 in FIG. 1A when a sample 104 with a first type of microorganism (e.g. *Liberibacter crescens*) is exposed to the MEA 102. The second trace 306b is the action potential signal generated by the MEA 102 in FIG. 1A when a sample 104 with a second type of microorganism (e.g. *Pseudomonas aeruginosa*) is exposed to the MEA 102. The third trace 306c is the action potential signal generated by the MEA 102 in FIG. 1A when a sample 104 with a third type of microorganism (e.g. *Candidatus Liberibacter* spp) is exposed to the MEA 102. In some embodiments, the action potential signal is captured over a minimum time period 308. In one embodiment, the minimum time period 308 is sufficient to cover at least two cycles of the action potential signal. In another embodiment, the minimum time period 308 is approximately 20 ms.

During the initial storing phase, each trace 306 is transmitted from the MEA 102 to the controller 106 and the controller 106 generates the electrophysiological signature of each type of microorganism. The controller 106 then stores the electrophysiological signature of each type of microorganism in the memory of the controller 106. In one embodiment, the controller 106 stores the electrophysiological signature of each type of microorganism in a separate record 202 of the data structure 200 (e.g. electrophysiological signature of the first trace 306*a* is stored in record 202*a*, electrophysiological signature of the second trace 306*b* is stored in record 202*b*, etc). Additionally, the controller stores data indicating the type of the microorganism of each trace 306 in the third field 208 data. In an example embodiment, data indicating the *Liberibacter crescens* bacteria present in the sample 104 generating the first trace 306*a* is stored in the third field 208*a* of the record 202*a*, data indicating the *Pseudomonas aeruginosa* bacteria present in the sample 104 generating the second trace 306*b* is stored in the third field 208*b* of the record 202*b*, etc.

FIG. 4B is an image that illustrates an example of a plot 400 including a growth curve 406 of a bacteria, according to an embodiment. The horizontal axis 402 is time in units of hours:minutes:seconds. The vertical axis 404 is absorbance in units of $OD_{600}$. As known by those skilled in the art, $OD_{600}$ is a common unit for estimating a concentration of bacteria or other cells in a liquid. In some embodiments, bacteria is present in the sample 104 and exposed to the MEA 102. At one or more stages 410 of the growth curve 406, the action potential signal is transmitted to the controller 106 and the electrophysiological signature of the sample 104 at those respective stages 410 is generated and stored in the memory of the controller 106. In other embodiments, the action potential signal is transmitted to the controller 106 at multiple time increments 408 over a time period and the electrophysiological signature of the sample 104 is generated at each time increment and stored in the memory. In an example embodiment, the time increment 408 is one hour and the time period is 24 hours. In some embodiments, data indicating the respective stage 410 is stored in the fourth field 210 of each record 202 of the data structure 200. During a first stage 410*a* of the growth curve 406 (e.g. lag stage), the electrophysiological signature of the sample 104 is generated by the controller 106 and stored in the data structure 200. During a second stage 410*b* of the growth curve 406 (e.g. exponential stage), the electrophysiological signature of the sample 104 is generated by the controller 106 and stored in the data structure 200. During a third stage 410*c* of the growth curve 406 (e.g. stationary stage), the electrophysiological signature of the sample 104 is generated by the controller 106 and stored in the data structure 200.

FIG. 4C is an image 420*a* that illustrates an example of electrical activity of the bacteria during the first stage 410*a* of the growth curve 406 of FIG. 4B, according to an embodiment. In some embodiments, the image 420*a* is a two-dimensional array of pixels 424 corresponding to a two-dimensional MEA 102. In this embodiment, each pixel 424 in a region of the image 420*a* indicates a value of the action potential from electrodes in a corresponding region of the MEA 102. The image 420*a* includes a scale 422*a* that indicates that the pixels 424 are coded based on the values of the action potential from the electrodes in the MEA 102. In one embodiment, the scale 422*a* extends from a low value (dark blue) of about 0 µV to a high value (white) of about 41 µV. In some embodiments, the pixels 424 of the image 420*a* indicate that the bacteria present in the sample 104 is dead, i.e. the level of electrical activity indicated by the pixels 424 is less than the threshold value of the bacteria being alive. In another embodiment, the pixels 424 of the image 420*a* indicate that the bacteria present in the sample 104 is in a non-replicating stage.

Figure 4D:
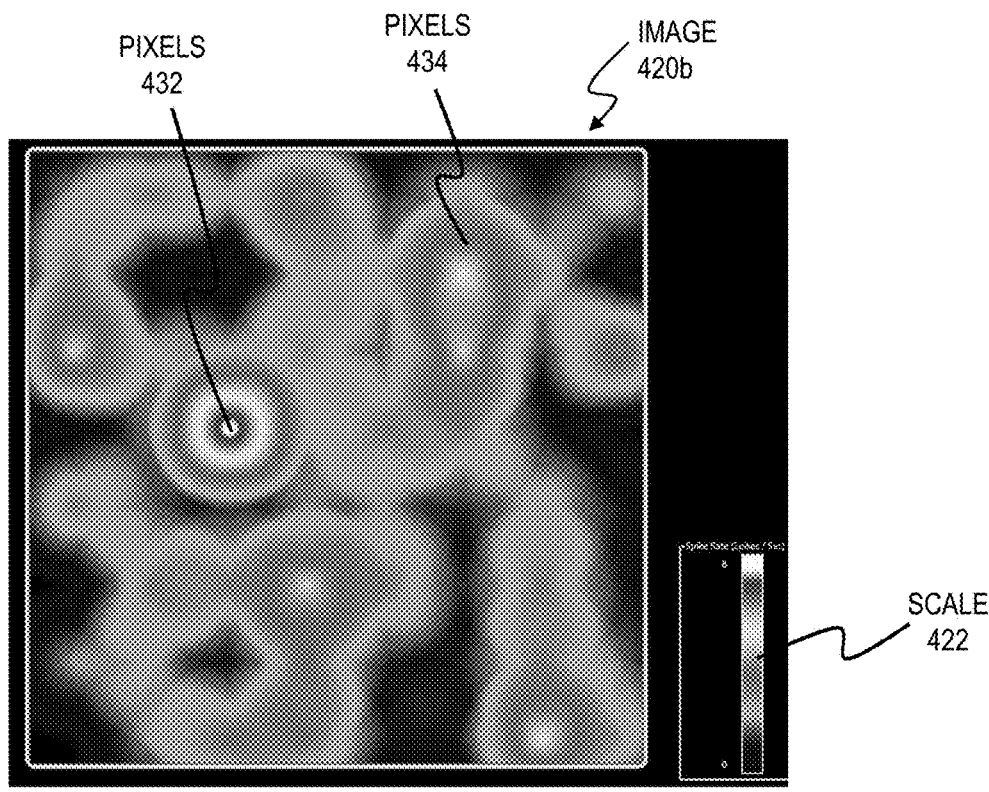
FIG. 4D is an image that illustrates an example of electrical activity of the bacteria during a second stage of the growth curve of FIG. 4B, according to an embodiment.

FIG. 4D is an image 420*b* that illustrates an example of electrical activity of the bacteria during the second stage 410*b* of the growth curve 406 of FIG. 4B, according to an embodiment. Based on the scale 422, a first group of pixels 432 on the image 420*b* indicate a region where high electrical activity of the bacteria is occurring and a second group of pixels 434 on the image 420*b* indicate a region where medium electrical activity of the bacteria is occurring. In one embodiment, the scale 422 extends from a low value (dark blue) of about 0 µV to a high value (white) of about 8 µV. In some embodiments, the pixels 432, 434 of the image 420*b* indicate that the bacteria present in the sample 104 is alive, i.e. the level of electrical activity indicated by the pixels 424 is above the threshold value that the bacteria is alive. In another embodiment, the pixels 432, 434 of the image 420*b* indicate that the bacteria present in the sample 104 is in a replicating stage.

Figure 4E:
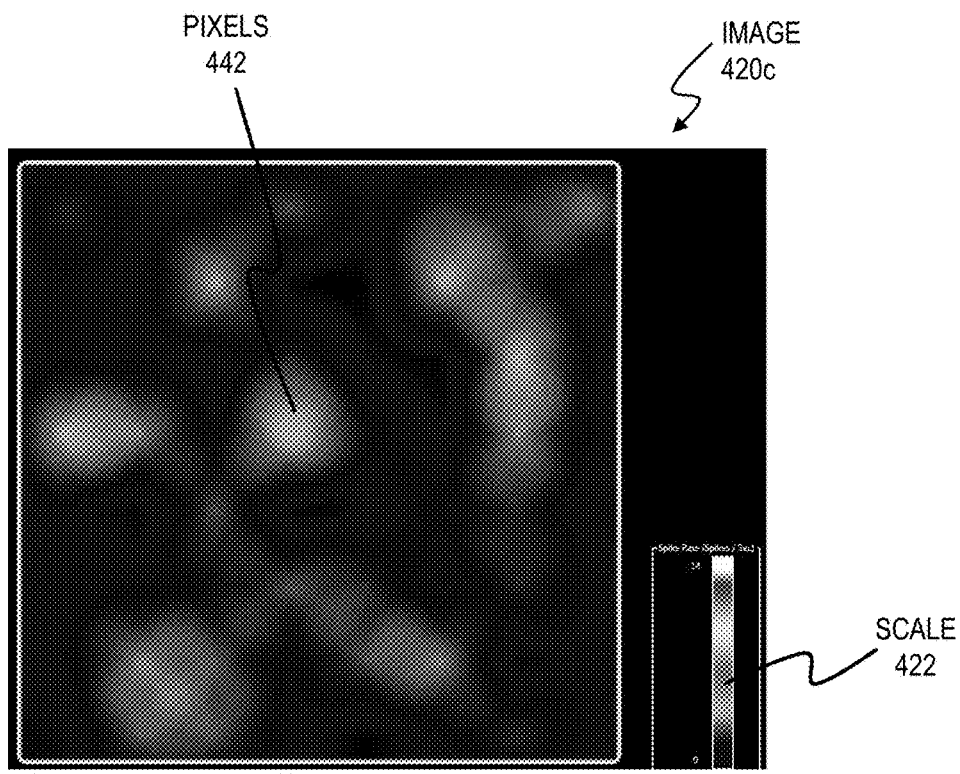
FIG. 4E is an image that illustrates an example of electrical activity of the bacteria during a third stage of the growth curve of FIG. 4B, according to an embodiment.

FIG. 4E is an image 420*c* that illustrates an example of electrical activity of the bacteria during the third stage 410*c* of the growth curve 406 of FIG. 4B, according to an embodiment. Based on the scale 422, pixels 442 on the image 420*c* indicate a region where the electrical activity of the bacteria is occurring and above the threshold value indicating the bacteria is alive. In one embodiment, the scale 422 extends from a low value (dark blue) of about 0 µV to a high value (white) of about 14 µV. In another embodiment, the pixels 442 of the image 420*c* indicate that the bacteria present in the sample 104 is in a non-replicating stage.

Figure 4F:
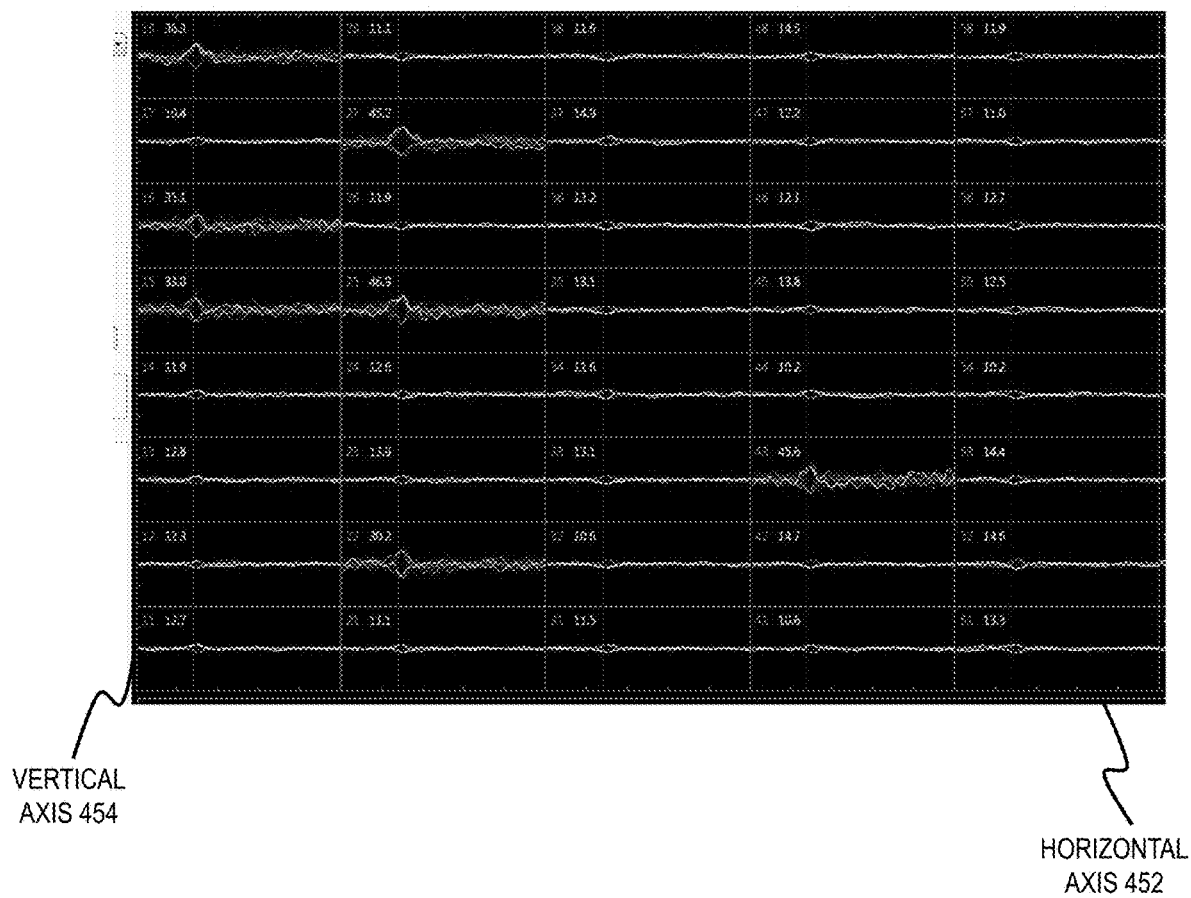
FIG. 4F is an image that illustrates an example of multiple signals received from the MEA of FIG. 1A, according to an embodiment.

FIG. 4F is an image that illustrates an example of a plot 450 of multiple signals received from the MEA 102 of FIG. 1A, according to an embodiment. The horizontal axis 452 is time in arbitrary units. The vertical axis 454 is potential amplitude in units of microvolts (µV). In some embodiments, the plot 450 depicts multiple action potential signals received by the controller 106 from multiple electrodes within the MEA 102. FIG. 4F depicts the amplitude of each action potential signal along the horizontal axis 452. In some embodiments, the controller 106 determines the average peak value of the multiple signals by averaging the peak values of the multiple signals over a time period. In other embodiments, the controller 106 determines the peak rate (e.g. average number of peaks per second) by determining the average peak rate of the multiple signals over the time period.

Although steps are depicted in FIGS. 5A-5B, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

FIG. 5A is a flow diagram that illustrates an example of a method 500 for determining a presence of a microorganism in a sample, according to an embodiment. In step 502, the electrophysiological and/or impedance signatures of a plurality of microorganisms are stored in a memory of the controller 106. In some embodiments, in step 502, a plurality of samples 104 are exposed to the MEA 102, where one or more parameters of the microorganism present in each sample 104 is known. In these embodiments, in step 502, the controller 106 generates an electrophysiological signature for each sample 104 and stores the electrophysiological signature in the memory of the controller 106. In these embodiments, in step 502, the controller 106 further stores data indicating one or more known parameters (e.g. type of microorganism, growth stage, live status, replicating status, treatment efficacy) in the memory of the controller 106. In some embodiments, in step 502, a plurality of samples 104 are exposed to the IDE 103, where one or more parameters of the microorganism present in each sample 104 is known. In these embodiments, in step 502, the controller 106 generates an impedance signature for each sample 104 and stores the impedance signature in the memory of the controller 106. In these embodiments, in step 502, the controller 106 further stores data indicating one or more known parameters (e.g. type of microorganism, growth stage, live status, replicating status, treatment efficacy) in the memory of the controller 106. In yet other embodiments, in step 502, the electrophysiological and impedance signatures are generated by the controller 106 and stored in the memory of the controller 106. In an embodiment, each sample 104 is exposed to the IDE 126 and/or MEA 130 of the biosensor 150 using the microfluidic channel 128 after passing the sample 104 into the microfluidic ports 124*a*, 124*b*. In an example embodiments, in step 502 the biosensor 150 is positioned in an incubator at a fixed temperature (e.g. 37C) and rotated at a rotation speed (e.g. 150 rpm) to continuously shake the sample 104 within the microfluidic channel 128 as the IDE 126 and/or MEA 103 generates the impedance data and/or the action potential data. In other embodiments, the IDE 126 and/or the MEA 103 of the biosensor 150 gathers impedance data and/or action potential data from the sample 104 in the microfluidic channel 128 using these techniques for one or more other steps where impedance data and/or action potential data is gathered in the method of FIGS. 5A-5B.

In some embodiments, in step 502, the controller 106 stores the electrophysiological signature and/or impedance signature of each sample 104 in a respective record 202 of the data structure 200. In an example embodiment, in step 502, the controller 106 stores data indicating the values of the electrophysiological parameters (e.g. peak amplitude, peak rate) in fields 204, 206 of the data structure 200 and/or the values of the impedance parameters (e.g. peak impedance value, peak difference value, time value corresponding to the peak values, etc) in field 218 of the data structure 200. In other embodiments, the controller 106 stores data indicating a type of the microorganism (e.g. *Candidatus Liberibacter* spp, *Escherichia coli, Staphylococcus aureus*) in the third field 208 of the data structure 200. In other embodiments, the controller 106 stores data indicating a growth stage of the microorganism (e.g. exponential stage) in the fourth field 210 of the data structure 200. In other embodiments, the controller 106 stores data indicating a live status of the microorganism (e.g. live or dead) in the fifth field 212 of the data structure 200. In other embodiments, the controller 106 stores data indicating a replicating status of the microorganism (e.g. replicating or non-replicating) in the sixth field 214 of the data structure 200. In other embodiments, the controller 106 stores data indicating the treatment efficacy (e.g. drug resistant or drug susceptible) in the seventh field 216 of the data structure 200.

In step 502, in some embodiments, multiple electrophysiological signatures and/or multiple impedance signatures are stored in the memory for each microorganism. In these embodiments, an electrophysiological signature and/or impedance signature of a pure culture of the microorganism is generated and stored in the memory of the controller 106. In another embodiment, an electrophysiological signature and/or impedance signature of the microorganism in the presence of a sample (e.g. leaf extract) is generated and stored in the memory of the controller 106. In yet another embodiment, an electrophysiological signature and/or impedance signature of the microorganism after treatment (e.g. post-antibiotic) is generated and stored in the memory of the controller 106.

In step 502, in other embodiments, multiple electrophysiological signatures and/or multiple impedance signatures are stored in the memory for multiple samples (e.g. leaf extract) in the absence of any microorganism. In these embodiments, the multiple electrophysiological signatures and/or multiple impedance signatures are generated and stored in the memory of the controller 106. These signatures can be used to advantageously identify whether an unknown sample is absent of a microorganism, based on a match between the electrophysiological signature and/or impedance signature of the unknown sample and the stored electrophysiological signature and/or impedance signature.

In step 502, in other embodiments, a plurality of impedance signatures of a plurality of microorganisms are stored in the memory of the controller 106. The impedance signatures are generated and stored in a similar manner as the electrophysiological signatures, with the exception that the impedance signatures are based on the impedance signal generated by the IDE 103.

In step 504, the sample 104 is obtained. In some embodiments, a presence of microorganisms in the sample 104 obtained in step 504 is unknown. This is distinct from the samples 104 in step 502, where the microorganism present in the sample 104 is known and the electrophysiological signature and/or impedance signature of the sample 104 is stored in the memory along with one or more parameters of the known microorganism. In some embodiments, the sample 104 is obtained in step 504 using any techniques known to one of ordinary skill in the art. In an embodiment, where the sample 104 is obtained from a plant (e.g. citrus tree), the sample 104 includes leaf extract and/or phloem sap. In this example embodiment, the sample 104 (e.g. leaf extract) is obtained from the plant using a sample mesh bag manufactured by AGDIA® of Elkhart, Ind. In other embodiments, where the sample 104 is a liquid (e.g. bacterial growth media) that holds a bacteria microorganism and is passed through the microfluidic ports 124*a*, 124*b* and into the microfluidic passage 128, the IDE 126 and/or the MEA gather impedance data and/or action potential data of the sample 104 over a time period. In an embodiment, the biosensor 150 is positioned in an incubator with a temperature (e.g. 37C) and rotated with a rotation speed (e.g. 150 rpm) during the time period that the impedance data and/or action potential data is gathered.

In step 504, in one embodiment, a threshold amount of the sample 104 is obtained. In some embodiments, the threshold amount of the sample 104 is obtained for purposes of achieving a meaningful comparison with the electrophysiological signatures and/or impedance signatures of the samples 104 used in step 502.

In step 506, the electrophysiological signature and/or impedance signature is generated of the sample 104 obtained in step 504. In some embodiments, the controller 106 generates the electrophysiological signature of the sample 104, based on the action potential signal received from the MEA 102. In another embodiment, in step 506, an impedance signature is generated by the controller 106 of the sample 104, based on an impedance signal generated by the electrodes of the IDE 126 and received by the controller 106.

In step 508, the electrophysiological signature and/or impedance signature of the sample 104 generated in step 506 is compared with the stored electrophysiological signatures and/or impedance signatures in the memory of the controller 106. In some embodiments, the average peak value of the electrophysiological signature of the sample 104 generated in step 506 is compared with the stored average peak values of the electrophysiological signatures in the memory of the controller 106. In other embodiments, the peak rate of the electrophysiological signature of the sample 104 generated in step 506 is compared with the stored peak rates of the electrophysiological signatures in the memory of the controller 106. In still other embodiments, one or more other parameter values of the electrophysiological signature of the sample 104 generated in step 506 is compared with the stored parameter values of the electrophysiological signatures in the memory of the controller 106. In other embodiments, a peak value of the impedance signal or a peak difference value of the impedance signals of the sample 104 generated in step 506 is compared with the stored peak values of the impedance signals or the peak difference values of the impedance signals of the impedance signatures in the memory of the controller 106.

In some embodiments, in step 508, the electrophysiological signature and/or impedance signature of the sample 104 generated in step 506 is compared with the stored electrophysiological signatures and/or impedance signatures in the data structure 200. In some embodiments, the average peak value of the electrophysiological signature of the sample 104 generated in step 506 is compared with the first field 204 data of each stored electrophysiological signature in the data structure 200. In other embodiments, the peak rate of the electrophysiological signature of the sample 104 generated in step 506 is compared with the second field 206 data of the stored electrophysiological signatures in the data structure 200. In still other embodiments, one or more other parameter values of the electrophysiological signature of the sample 104 generated in step 506 is compared with other field data of the electrophysiological signatures in the data structure 200. In other embodiments, a peak value of the impedance signal or a peak value of the difference of the impedance signals of the sample 104 generated in step 506 is compared with the stored peak values of the impedance signals or the peak values of the difference of the impedance signals of the impedance signatures in the eighth field 218 of each record 202 in the data structure 200.

In step 508, in other embodiments, the impedance signature of the sample 104 generated in step 506 is compared with the stored impedance signatures in the memory of the controller 106.

In step 510, a presence of a microorganism in the sample 104 is identified. In some embodiments, the presence of the microorganism in the sample 104 is identified based on an identified correlation between the electrophysiological and/or impedance signature of the sample 104 and one of the stored electrophysiological and/or impedance signatures in the memory of the controller 106. In other embodiments, the presence of the microorganism in the sample 104 is identified based on an identified correlation between the electrophysiological and/or impedance signature of the sample 104 and one of the stored electrophysiological and/or impedance signatures in the data structure 200. In one embodiment, the correlation is identified during the comparison of step 508. In an example embodiment, the correlation is based on a value of one or more parameters of the electrophysiological and/or impedance signature of the sample 104 being within a threshold of the value of one or more parameters of the stored electrophysiological and/or impedance signatures in the memory of the controller 106. In an example embodiment, the threshold is in a range of 5-10%.

In step 510, in other embodiments, a quantity of one of the microorganisms in the sample 104 is identified based on an identified correlation between the impedance signature of the sample 104 and one of the stored impedance signatures in the memory of the controller 106.

In some embodiments, in step 510, a live status (e.g. alive or dead) of the present microorganism in the sample 104 is also identified. In these embodiments, when the controller 106 correlates the electrophysiological and/or impedance signature of the sample 104 with one of the stored electrophysiological and/or impedance signatures in the memory of the controller 106, the controller 106 retrieves a stored live status (e.g. alive or dead) corresponding to the stored electrophysiological signature from the memory of the controller 106. In other embodiments, where the controller 106 correlates the electrophysiological and/or impedance signature of the sample 104 with one of the records 202 in the data structure 200, the controller 106 retrieves data from the fifth field 212 indicating the live status of the microorganism.

In some embodiments, in step 510, a replicating status (e.g. replicating or non-replicating) of the present microorganism in the sample 104 is also identified. In these embodiments, when the controller 106 correlates the electrophysiological and/or impedance signature of the sample 104 with one of the stored electrophysiological and/or impedance signatures in the memory of the controller 106, the controller 106 retrieves a stored replicating status (e.g. replicating or non-replicating) corresponding to the stored electrophysiological and/or impedance signature from the memory of the controller 106. In other embodiments, where the controller 106 correlates the electrophysiological and/or impedance signature of the sample 104 with one of the records 202 in the data structure 200, the controller 106 retrieves data from the sixth field 214 indicating the replicating status of the microorganism.

In some embodiments, the method includes a step where an output is presented on the display 108 that indicates the identified presence of the microorganism in the sample 104 from step 510. In one embodiment, the identified presence of the microorganism output on the display 108 includes one or more known parameters (e.g. type of microorganism, growth stage, live status, replicating status, treatment efficacy) of the stored electrophysiological and/or impedance signature of the microorganism stored in the memory of the controller 106. In other embodiments, the identified presence of the microorganism output on the display 108 includes data from one or more of the fields 208, 210, 212, 214, 216, 218 of the electrophysiological and/or impedance signature for the identified microorganism stored in the record 202.

In other embodiments, the method includes a step where the output on the display 108 further includes identifying a treatment based on the identified presence of the microorganism in the sample 104 from step 510. In some embodiments, the identified treatment is based on a treatment efficacy of the identified microorganism that is stored in the memory of the controller 106. In other embodiments, the identified treatment is based on data of the seventh field 216

(e.g. treatment efficacy) of the record 202 corresponding to the identified microorganism. In an embodiment, the treatment is for the source of the sample 104 (e.g. tree).

In some embodiments, the method further includes treating the source of the sample 104 (e.g. tree) with the identified treatment. In an example embodiment, the identified treatment used to treat bacteria in a plant (e.g. HLB in a citrus tree) includes copper based pesticides, zinc based pesticides or a combination. In another example embodiment, the identified treatment used to treat bacteria in a plant (e.g. HLB in a citrus tree) includes antibiotics such as Streptomycin and Oxytetracycline. In other embodiments, the treatment also includes thermal therapy and any other chemical and physical based therapies to kill the HLB bacteria. In an embodiment, after waiting a period of time, a second sample 104 is obtained from the source and the electrophysiological and/or impedance signature of the second sample 104 is generated. The controller 106 compares the electrophysiological and/or impedance signature of the second sample 104 with the electrophysiological and/or impedance signature of the first sample 104, to confirm an efficacy of the treatment.

FIG. 5B is a flow diagram that illustrates an example of a method 550 for determining a presence of a growth stage of a microorganism in a sample, according to an embodiment. In step 552, the electrophysiological and/or impedance signatures of a plurality of growth stages of the microorganism are stored in a memory of the controller 106. In some embodiments, in step 552, the sample 104 includes a known microorganism (e.g. bacteria) and is exposed to the MEA 102 or IDE 103 over a time period and the electrophysiological and/or impedance signature at different stages of a growth curve (e.g. 410a, 410b, 410c in FIG. 4B) are generated. In these embodiments, in step 552, the controller 106 generates an electrophysiological and/or impedance signature for each growth stage and stores the electrophysiological and/or impedance signatures in the memory of the controller 106. In these embodiments, in step 552, the controller 106 further stores data indicating one or more known parameters (e.g. type of microorganism, live status, replicating status, treatment efficacy) in the memory of the controller 106. In some embodiments, the controller 106 stores the electrophysiological and/or impedance signature of each growth stage in a respective record 202 of the data structure 200. In an example embodiment, in step 552, the controller 106 stores data indicating the values of the electrophysiological parameters (e.g. peak amplitude, peak rate) in fields 204, 206 of the data structure 200 and/or values of the impedance parameters (e.g. peak impedance value, peak difference value, slope value, etc) in field 218 of the data structure 200. In other embodiments, the controller 106 stores data indicating the type of the microorganism (e.g. *Candidatus Liberibacter* spp, *Escherichia coli, Staphylococcus aureus*) in the third field 208 of the data structure 200. In other embodiments, the controller 106 stores data indicating the growth stage (e.g. exponential stage) in the fourth field 210 of the data structure 200. In other embodiments, the controller 106 stores data indicating the live status of the growth stage (e.g. live or dead) in the fifth field 212 of the data structure 200. In other embodiments, the controller 106 stores data indicating a replicating status of the growth stage (e.g. replicating or non-replicating) in the sixth field 214 of the data structure 200. In other embodiments, the controller 106 stores data indicating the treatment efficacy (e.g. drug resistant or drug susceptible) in the seventh field 216 of the data structure 200.

Steps 554, 556, 558 are similar to steps 504, 506, 508 discussed previously.

In step 560, a presence of a growth stage in the sample 104 obtained in step 504 is identified. In some embodiments, the presence of the growth stage of the sample 104 is identified based on an identified correlation between the electrophysiological and/or impedance signature of the sample 104 and one of the stored electrophysiological and/or impedance signatures from step 552 in the memory of the controller 106. In other embodiments, the presence of the growth stage in the sample 104 is identified based on an identified correlation between the electrophysiological and/or impedance signature of the sample 104 and one of the stored electrophysiological and/or impedance signatures in the data structure 200. In one embodiment, the correlation is identified during the comparison of step 558. In an example embodiment, the correlation is based on a value of one or more parameters of the electrophysiological and/or impedance signature of the sample 104 being within a threshold of the value of one or more parameters of the stored electrophysiological and/or impedance signatures in the memory of the controller 106. In an example embodiment, the threshold is in a range of 5-10%.

2. Hardware Overview

FIG. 6 is a block diagram that illustrates a computer system 600 upon which an embodiment of the invention may be implemented. Computer system 600 includes a communication mechanism such as a bus 610 for passing information between other internal and external components of the computer system 600. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 600, or a portion thereof, constitutes a means for performing one or more steps of one or more methods described herein.

A sequence of binary digits constitutes digital data that is used to represent a number or code for a character. A bus 610 includes many parallel conductors of information so that information is transferred quickly among devices coupled to the bus 610. One or more processors 602 for processing information are coupled with the bus 610. A processor 602 performs a set of operations on information. The set of operations include bringing information in from the bus 610 and placing information on the bus 610. The set of operations also typically include comparing two or more units of information, shifting positions of units of information, and combining two or more units of information, such as by addition or multiplication. A sequence of operations to be executed by the processor 602 constitutes computer instructions.

Computer system 600 also includes a memory 604 coupled to bus 610. The memory 604, such as a random access memory (RAM) or other dynamic storage device, stores information including computer instructions. Dynamic memory allows information stored therein to be changed by the computer system 600. RAM allows a unit of information stored at a location called a memory address to be stored and retrieved independently of information at neighboring addresses. The memory 604 is also used by the processor 602 to store temporary values during execution of computer instructions. The computer system 600 also includes a read only memory (ROM) 606 or other static storage device coupled to the bus 610 for storing static information, including instructions, that is not changed by the computer system 600. Also coupled to bus 610 is a non-volatile (persistent) storage device 608, such as a magnetic disk or optical disk, for storing information, including instructions, that persists even when the computer system 600 is turned off or otherwise loses power.

Information, including instructions, is provided to the bus 610 for use by the processor from an external input device 612, such as a keyboard containing alphanumeric keys operated by a human user, or a sensor. A sensor detects conditions in its vicinity and transforms those detections into signals compatible with the signals used to represent information in computer system 600. Other external devices coupled to bus 610, used primarily for interacting with humans, include a display device 614, such as a cathode ray tube (CRT) or a liquid crystal display (LCD), for presenting images, and a pointing device 616, such as a mouse or a trackball or cursor direction keys, for controlling a position of a small cursor image presented on the display 614 and issuing commands associated with graphical elements presented on the display 614.

In the illustrated embodiment, special purpose hardware, such as an application specific integrated circuit (IC) 620, is coupled to bus 610. The special purpose hardware is configured to perform operations not performed by processor 602 quickly enough for special purposes. Examples of application specific ICs include graphics accelerator cards for generating images for display 614, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 600 also includes one or more instances of a communications interface 670 coupled to bus 610. Communication interface 670 provides a two-way communication coupling to a variety of external devices that operate with their own processors, such as printers, scanners and external disks. In general the coupling is with a network link 678 that is connected to a local network 680 to which a variety of external devices with their own processors are connected. For example, communication interface 670 may be a parallel port or a serial port or a universal serial bus (USB) port on a personal computer. In some embodiments, communications interface 670 is an integrated services digital network (ISDN) card or a digital subscriber line (DSL) card or a telephone modem that provides an information communication connection to a corresponding type of telephone line. In some embodiments, a communication interface 670 is a cable modem that converts signals on bus 610 into signals for a communication connection over a coaxial cable or into optical signals for a communication connection over a fiber optic cable. As another example, communications interface 670 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 670 sends and receives electrical, acoustic or electromagnetic signals, including infrared and optical signals, that carry information streams, such as digital data.

The term computer-readable medium is used herein to refer to any medium that participates in providing information to processor 602, including instructions for execution. Such a medium may take many forms, including, but not limited to, non-volatile media, volatile media and transmission media. Non-volatile media include, for example, optical or magnetic disks, such as storage device 608. Volatile media include, for example, dynamic memory 604. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 602, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 602, except for carrier waves and other signals.

Logic encoded in one or more tangible media includes one or both of processor instructions on a computer-readable storage media and special purpose hardware, such as ASIC *620.

Network link 678 typically provides information communication through one or more networks to other devices that use or process the information. For example, network link 678 may provide a connection through local network 680 to a host computer 682 or to equipment 684 operated by an Internet Service Provider (ISP). ISP equipment 684 in turn provides data communication services through the public, world-wide packet-switching communication network of networks now commonly referred to as the Internet 690. A computer called a server 692 connected to the Internet provides a service in response to information received over the Internet. For example, server 692 provides information representing video data for presentation at display 614.

The invention is related to the use of computer system 600 for implementing the techniques described herein. According to one embodiment of the invention, those techniques are performed by computer system 600 in response to processor 602 executing one or more sequences of one or more instructions contained in memory 604. Such instructions, also called software and program code, may be read into memory 604 from another computer-readable medium such as storage device 608. Execution of the sequences of instructions contained in memory 604 causes processor 602 to perform the method steps described herein. In alternative embodiments, hardware, such as application specific integrated circuit 620, may be used in place of or in combination with software to implement the invention. Thus, embodiments of the invention are not limited to any specific combination of hardware and software.

The signals transmitted over network link 678 and other networks through communications interface 670, carry information to and from computer system 600. Computer system 600 can send and receive information, including program code, through the networks 680, 690 among others, through network link 678 and communications interface 670. In an example using the Internet 690, a server 692 transmits program code for a particular application, requested by a message sent from computer 600, through Internet 690, ISP equipment 684, local network 680 and communications interface 670. The received code may be executed by processor 602 as it is received, or may be stored in storage device 608 or other non-volatile storage for later execution, or both. In this manner, computer system 600 may obtain application program code in the form of a signal on a carrier wave.

Various forms of computer readable media may be involved in carrying one or more sequence of instructions or data or both to processor 602 for execution. For example, instructions and data may initially be carried on a magnetic disk of a remote computer such as host 682. The remote computer loads the instructions and data into its dynamic memory and sends the instructions and data over a telephone line using a modem. A modem local to the computer system 600 receives the instructions and data on a telephone line and uses an infra-red transmitter to convert the instructions and data to a signal on an infra-red a carrier wave serving as the network link 678. An infrared detector serving as communications interface 670 receives the instructions and data carried in the infrared signal and places information representing the instructions and data onto bus 610. Bus 610 carries the information to memory 604 from which processor 602 retrieves and executes the instructions using some of the data sent with the instructions. The instructions and data received in memory 604 may optionally be stored on storage device 608, either before or after execution by the processor 602.

FIG. 7 illustrates a chip set 700 upon which an embodiment of the invention may be implemented. Chip set 700 is programmed to perform one or more steps of a method described herein and includes, for instance, the processor and memory components described with respect to FIG. *6 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 700, or a portion thereof, constitutes a means for performing one or more steps of a method described herein.

In one embodiment, the chip set 700 includes a communication mechanism such as a bus 701 for passing information among the components of the chip set 700. A processor 703 has connectivity to the bus 701 to execute instructions and process information stored in, for example, a memory 705. The processor 703 may include one or more processing cores with each core configured to perform independently. A multi-core processor enables multiprocessing within a single physical package. Examples of a multi-core processor include two, four, eight, or greater numbers of processing cores. Alternatively or in addition, the processor 703 may include one or more microprocessors configured in tandem via the bus 701 to enable independent execution of instructions, pipelining, and multithreading. The processor 703 may also be accompanied with one or more specialized components to perform certain processing functions and tasks such as one or more digital signal processors (DSP) 707, or one or more application-specific integrated circuits (ASIC) 709. A DSP 707 typically is configured to process real-world signals (e.g., sound) in real time independently of the processor 703. Similarly, an ASIC 709 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 703 and accompanying components have connectivity to the memory 705 via the bus 701. The memory 705 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 705 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

What is claimed is:

1. A method comprising:
storing, in a memory of a processor, electrophysiological signatures and impedance signatures of a plurality of microorganisms;
positioning a sample in a microfluidic channel that moves the sample to a microelectrode array (MEA) and an interdigitated electrode (IDE), wherein the MEA and the IDE are on different sides of the microfluidic channel within a microfluidic device;
generating an electrophysiological signature from the MEA and an impedance signature from the IDE simultaneously;
comparing, with the processor, the electrophysiological signature and the impedance signature of the sample with the electrophysiological signatures and impedance signatures in the memory; and
identifying, with the processor, a presence of one of the plurality of microorganisms in the sample based on a correlation between the at least one of the electrophysiological signature and the impedance signature of the sample and the electrophysiological signatures and the impedance signatures stored in the memory.

2. The method of claim 1, further comprising outputting, on a display, data indicating the presence of the one of the plurality of microorganism in the sample.

3. The method of claim 1, wherein the electrophysiological signatures comprise a value of at least one electrophysiological parameter of a potential signal from the MEA over a time period, wherein the electrophysiological parameter comprises an average peak amplitude or an average number of peaks per second, or both.

4. The method of claim 1, wherein the plurality of microorganisms comprise bacteria.

5. The method of claim 1, wherein the sample is obtained from a plant, an animal, or human bodily fluids.

6. The method of claim 5, wherein the plant is a citrus tree and the plurality of microorganisms include *Candidatus Liberibacter* asiaticus bacteria.

7. The method of claim 1, wherein the storing step comprises:
   obtaining a pure sample of each of the plurality of microorganisms;
   generating, with the plurality of electrodes, an electrophysiological signature and/or an impedance signature for each pure sample; and
   storing, in the memory of the processor, the electrophysiological signature and/or the impedance signature for each pure sample.

8. The method of claim 1, wherein said electrophysiological signatures of the storing step comprises at least one first electrophysiological signature of a live microorganism and at least one second electrophysiological signature of a dead microorganism; and
   wherein said identifying comprises identifying a presence of the live microorganism in the sample based on a correlation between the electrophysiological signature of the sample and the first electrophysiological signature and identifying a presence of the dead microorganism in the sample based on a correlation between the electrophysiological signature of the sample and the second electrophysiological signature.

9. The method of claim 1, wherein the impedance signature of the sample comprises a value of an impedance signal from the IDE over a time period.

10. The method of claim 9, wherein the storing the impedance signatures comprises:
    obtaining a plurality of samples, wherein each sample of the plurality of samples corresponds to a microorganism of the plurality of microorganisms;
    for each sample of the plurality of samples:
       generating, with the IDE, the value of a first impedance signal over the time period for the sample including the corresponding microorganism;
       generating, with the IDE, the value of a second impedance signal over the time period for a control sample excluding the corresponding microorganism;
       determining a peak of a difference between the value of the first impedance signal and the value of the second impedance signal; and
       storing, in the memory of the processor, the value of the peak of the difference.

11. A method for determining a presence of a microorganism in a sample, comprising:
    positioning the sample in a microfluidic channel that moves the sample to an MEA and an IDE, wherein the MEA and IDE are on different sides of the microfluidic channel within a microfluidic device;
    generating an electrophysiological signature and impedance signature of the sample simultaneously;
    comparing the electrophysiological signature and impedance signature of the sample with a database comprising electrophysiological signatures and impedance signatures corresponding to a plurality of microorganisms; and
    identifying a presence of one of the plurality of the microorganisms in the sample based on the comparison.

12. The method of claim 11, wherein the electrophysiological signature comprises a value of a potential signal from the MEA over a time period, or an average number of peaks per second of the action potential signal over the time period.

13. The method of claim 11, wherein the microorganism is bacteria.

14. The method of claim 11, wherein the sample is obtained from a plant.

* * * * *